United States Patent
Saito

(10) Patent No.: US 12,022,993 B2
(45) Date of Patent: Jul. 2, 2024

(54) ENDOSCOPE

(71) Applicant: OLYMPUS CORPORATION, Tokyo (JP)

(72) Inventor: Hidetoshi Saito, Hanno (JP)

(73) Assignee: OLYMPUS CORPORATION, Tokyo (JP)

( * ) Notice: Subject to any disclaimer, the term of this patent is extended or adjusted under 35 U.S.C. 154(b) by 639 days.

(21) Appl. No.: 16/941,978

(22) Filed: Jul. 29, 2020

(65) Prior Publication Data

US 2020/0352412 A1 Nov. 12, 2020

Related U.S. Application Data

(63) Continuation of application No. PCT/JP2018/031223, filed on Aug. 23, 2018.

(30) Foreign Application Priority Data

Feb. 5, 2018 (JP) .................................. 2018-018086

(51) Int. Cl.
*A61B 1/005* (2006.01)
*A61B 1/00* (2006.01)

(52) U.S. Cl.
CPC ........ *A61B 1/00078* (2013.01); *A61B 1/0051* (2013.01)

(58) Field of Classification Search
CPC . A61B 1/00071; A61B 1/00078; A61B 1/012; A61B 1/018; A61B 1/005; A61B 1/0051; A61B 1/0052; A61B 1/0056; A61B 1/0057

See application file for complete search history.

(56) References Cited

U.S. PATENT DOCUMENTS

| | | | | |
|---|---|---|---|---|
| 5,885,208 A | * | 3/1999 | Moriyama | ........... A61B 1/0051 600/146 |
| 2002/0188174 A1 | | 12/2002 | Aizawa et al. | |
| 2007/0043261 A1 | * | 2/2007 | Watanabe | .......... A61B 1/00071 600/152 |

(Continued)

FOREIGN PATENT DOCUMENTS

| | | | |
|---|---|---|---|
| JP | S63-115532 A | 5/1988 | |
| JP | H11-267090 A | 10/1999 | |

(Continued)

OTHER PUBLICATIONS

International Search Report dated Nov. 27, 2018 issued in PCT/JP2018/031223.

*Primary Examiner* — Ryan N Henderson
(74) *Attorney, Agent, or Firm* — Scully, Scott, Murphy & Presser, P.C.

(57) ABSTRACT

An endoscope includes: a coil spring which is helically wound around an outer periphery of a treatment instrument channel disposed in an insertion section, the coil spring including a distal end which is fixed to the insertion section on a distal end portion side with respect to a bending portion; and a slide member disposed on a proximal end side of the coil spring, the slide member provided for applying an operation force for deforming the coil spring so as to increase a bending strength of at least a portion of the coil spring corresponding to the inside of the bending portion.

19 Claims, 18 Drawing Sheets

(56) References Cited

U.S. PATENT DOCUMENTS

| | | | | |
|---|---|---|---|---|
| 2014/0188081 A1* | 7/2014 | Saito | ................. | A61B 1/00073 604/525 |
| 2015/0272425 A1* | 10/2015 | Ueda | ................. | A61B 1/00078 600/144 |
| 2017/0254447 A1* | 9/2017 | Saito | ................. | A61M 25/0053 |

FOREIGN PATENT DOCUMENTS

| | | | | | |
|---|---|---|---|---|---|
| JP | 2000-166860 A | | 6/2000 | | |
| JP | 2002360504 A | * | 12/2002 | ......... | A61B 1/00078 |
| JP | 2007-054125 A | | 3/2007 | | |
| JP | 2007-325794 A | | 12/2007 | | |

* cited by examiner

ENDOSCOPE

CROSS REFERENCE TO RELATED APPLICATION

This application is a continuation application of PCT/JP2018/031223 filed on Aug. 23, 2018 and claims benefit of Japanese Application No. 2018-018086 filed in Japan on Feb. 5, 2018, the entire contents of which are incorporated herein by this reference.

BACKGROUND OF THE INVENTION

1. Field of the Invention

The present invention relates to an endoscope provided with a bending portion on a distal end side of an insertion section.

2. Description of the Related Art

Conventionally, an endoscope has been used for performing observation of a target part in a subject and various treatments using a treatment instrument inserted into a treatment instrument channel when necessary by inserting an elongated insertion section into the subject such as a body cavity.

As this type of endoscope, a flexible endoscope where a distal end portion, a bending portion, and a flexible tube portion are arranged in this order from a distal end side has been widely used. In inserting the insertion section of the flexible endoscope in the subject, an operator of the endoscope (hereinafter simply referred to as "operator") grasps the operation section by one hand, and pushes the insertion section into the subject by grasping the flexible tube portion by the other hand. In such an operation, the operator operates operation levers or the like disposed on the operation section by the hand which grasps the operation section so as to bend the bending portion in a desired direction.

As such an endoscope, for example, there has been known a renal urological endoscope (renal pelvic ureter endoscope) having an insertion section which is insertable into a urethra, a ureter, a renal pelvis, or a renal calyx, for example. The ureter or the like is a fine and narrow lumen. As a technique for enhancing insertability of the insertion section, for example, Japanese Patent Application Laid-Open Publication No. 2007-325794 discloses a technique where a distal end cap for endoscope is detachably mounted on a distal end portion of an endoscope, and such a distal end cap for endoscope includes a cap portion having a tapered distal end surface with respect to a circular proximal end portion.

SUMMARY OF THE INVENTION

An endoscope according to an aspect of the present invention is an endoscope including: an insertion section being long and including a distal end portion and a proximal end portion, and provided with a bending portion between the distal end portion and the proximal end portion, the bending portion being bendable in a predetermined direction; a tubular member disposed in the insertion section; a wire-like member helically wound around an outer periphery of the tubular member, the wire-like member including a distal end which is fixed to the tubular member on a distal end portion side with respect to the bending portion; and an operation member disposed on a proximal end side of the wire-like member, the operation member being configured to deform the wire-like member so as to increase a bending strength of at least a portion of the wire-like member.

DETAILED DESCRIPTION OF THE PREFERRED EMBODIMENTS

Figure 1:
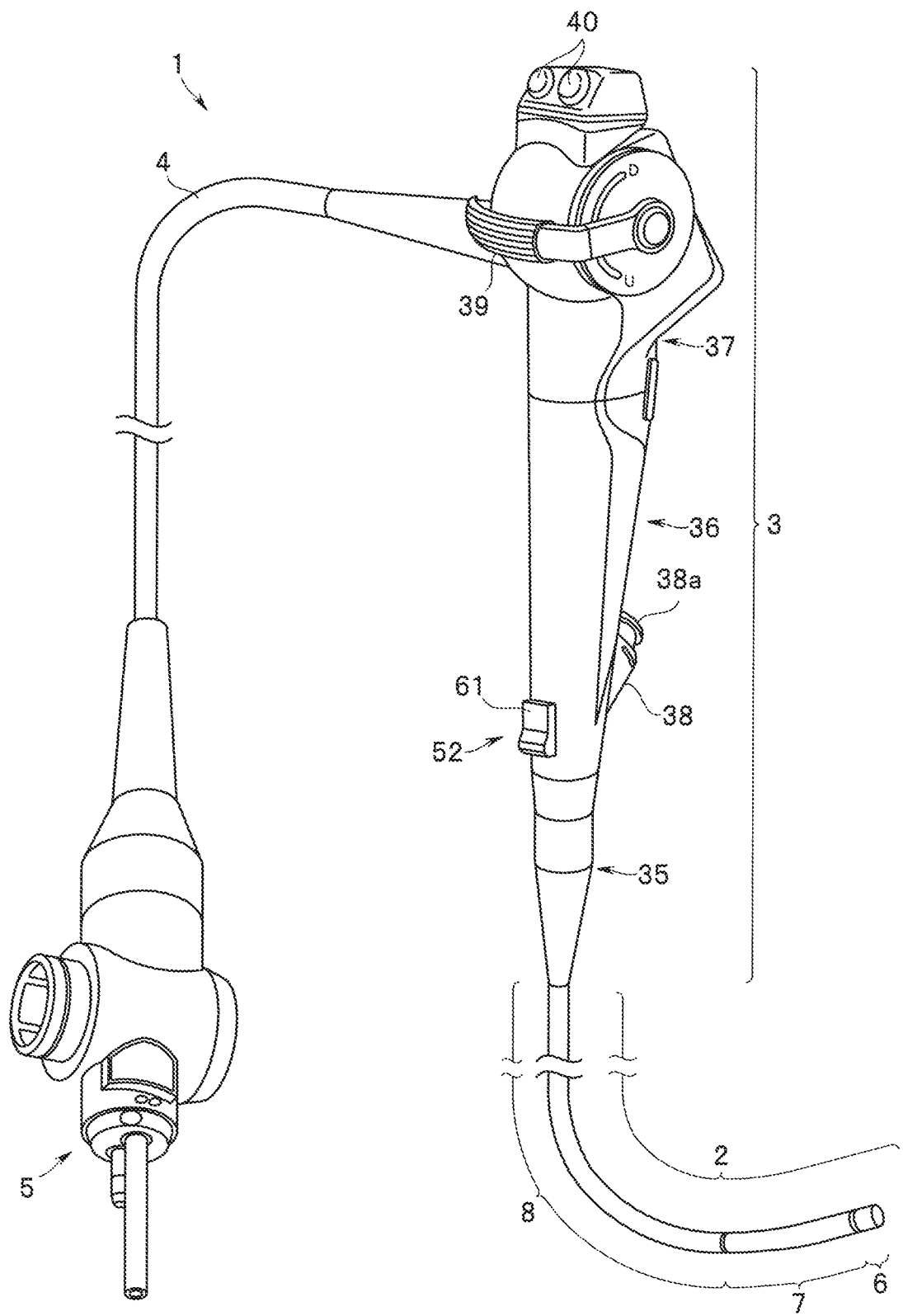
FIG. 1 is a perspective view showing an external appearance of an endoscope according to a first embodiment.
Figure 2:
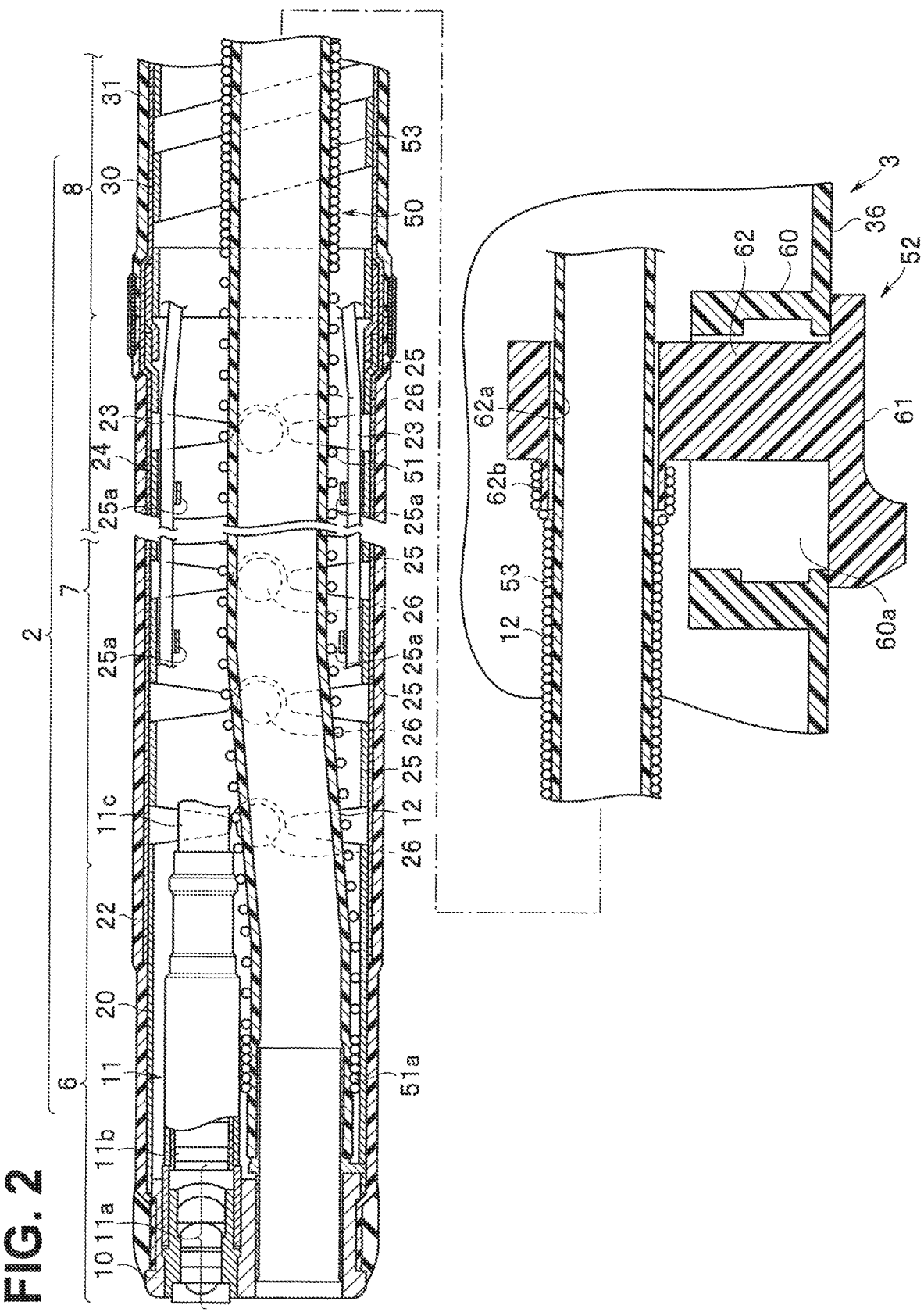
FIG. 2 is a cross-sectional view of a main part of an insertion section and an operation section in a state where a bending portion has a first bending strength in the first embodiment.
Figure 3:
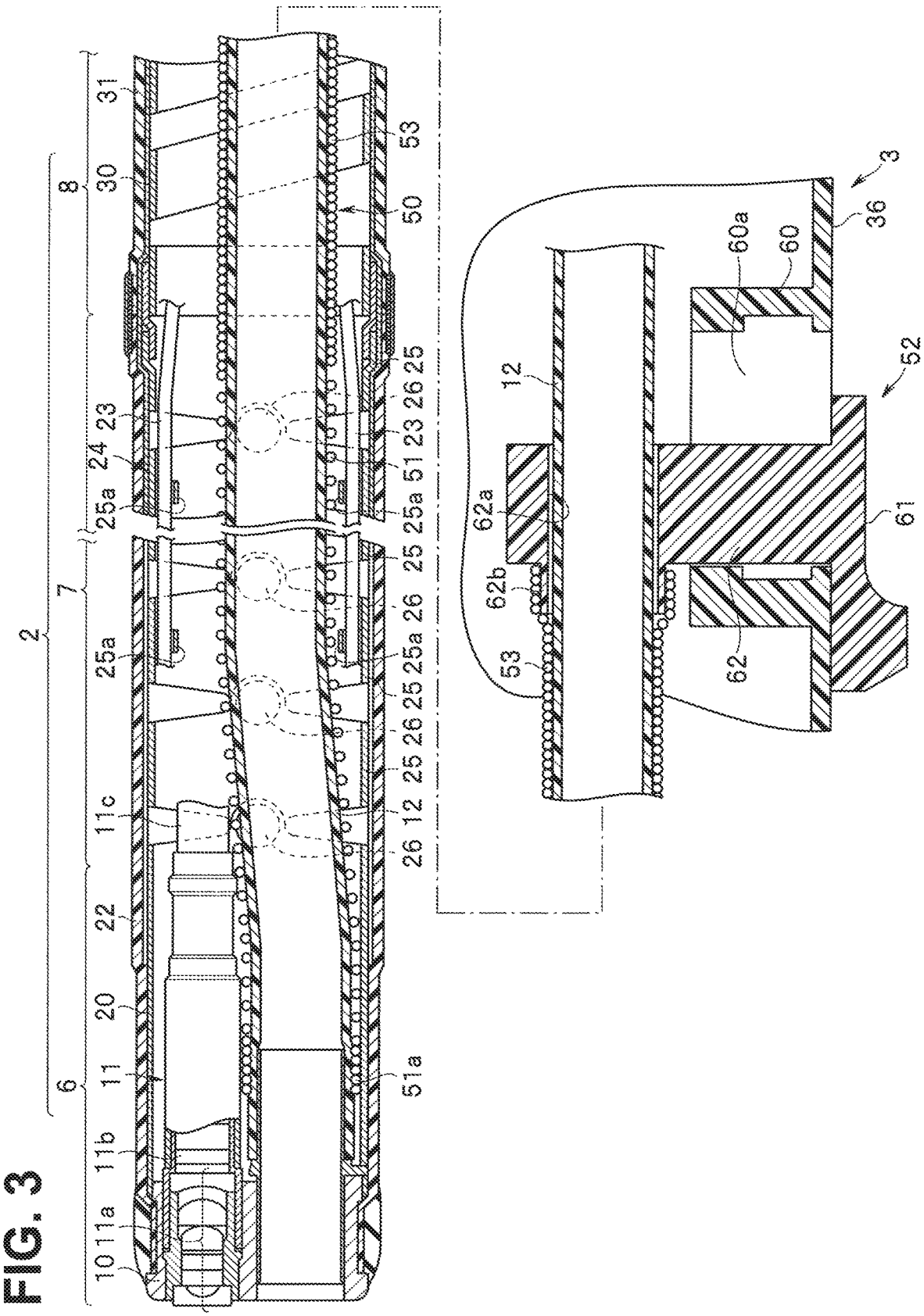
FIG. 3 is a cross-sectional view of the main part of the insertion section and the operation section in a state where a bending strength of the bending portion is a second bending strength higher than the first bending strength in the first embodiment.
Figure 4:
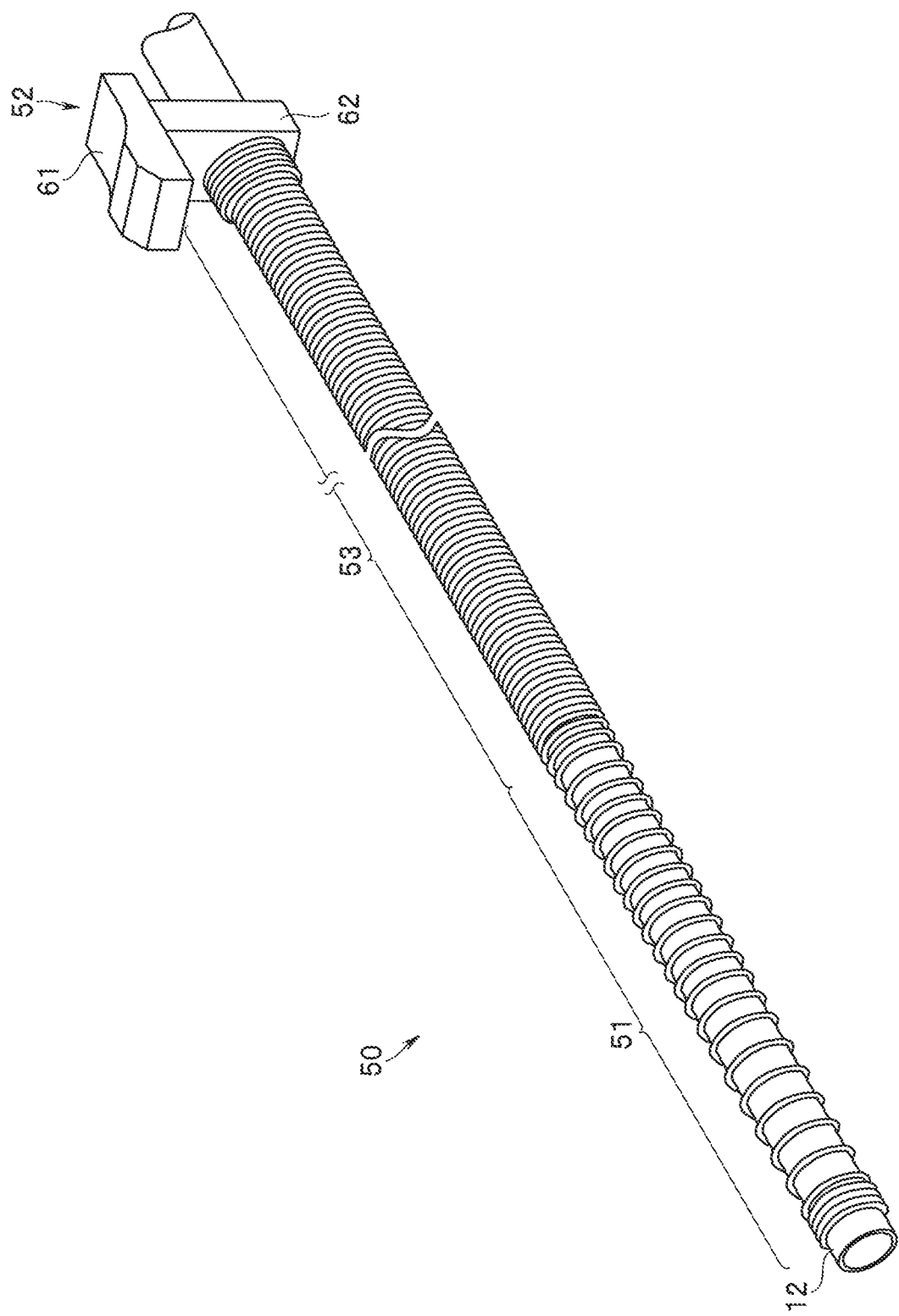
FIG. 4 is a perspective view showing a main part of a bending strength varying mechanism provided to a treatment instrument channel in the first embodiment.

Hereinafter, embodiments of the present invention are described with reference to drawings. FIG. 1 to FIG. 4 relate to a first embodiment of the present invention. FIG. 1 is a perspective view showing an external appearance of an endoscope, FIG. 2 is a cross-sectional view of a main part of an insertion section and an operation section in a state where a bending portion has a first bending strength, and FIG. 3 is a cross-sectional view of the main part of the insertion section and the operation section in a state where a bending strength of the bending portion is a second bending strength higher than the first bending strength, and FIG. 4 is a perspective view showing a main part of a bending strength varying mechanism provided to a treatment instrument channel.

An endoscope 1 shown in FIG. 1 is a renal urological endoscope (renal pelvic ureter endoscope), for example. The endoscope 1 includes: an insertion section 2 having an elongated shape (long length) which is inserted into a body cavity of a subject; an operation section 3 which is mounted on a proximal end of the insertion section 2; and a universal cable 4 which extends from a proximal end of the operation section 3.

As shown in FIG. 1, the insertion section 2 includes: a distal end portion 6 positioned on a distal end of the insertion section 2; a bending portion 7 continuously connected to a proximal end of the distal end portion 6; and a flexible tube portion 8 having flexibility and continuously connected to a proximal end of the bending portion 7.

As shown in FIGS. 2 and 3, a distal end rigid portion 10 made of metal is disposed in the distal end portion 6, and an image pickup unit 11, a light guide not shown, and a treatment instrument channel 12 which forms a tubular member are held in the distal end rigid portion 10. In such a configuration, the image pickup unit 11 has an image pickup optical system 11a, and an image pickup device 11b such as a CCD or a CMOS.

In the distal end portion 6, a distal-most end bending piece 20 having an approximately cylindrical shape which forms the bending portion 7 is fixed to a proximal end side of the distal end rigid portion 10. A pair of upper and lower wire fixing portions (not shown) is formed on an inner periphery of the distal-most end bending piece 20. Distal ends of two towing wires 23 which pass through the insertion section 2 are fixed to the respective wire fixing portions.

In the embodiment, in the distal end portion 6 (and the insertion section 2), for example, upward, downward, left-ward, and rightward directions are defined in correlation with an image picked up by the image pickup device 11b of the image pickup unit 11.

The bending portion 7 is configured to actively bend in the upward and downward directions in response to an operation input by an operator inputted to the operation section 3.

More specifically, the bending portion 7 of the embodiment has a bending piece set 24 where a plurality of bending pieces 25 are continuously connected in a row to a proximal end side of the distal-most end bending piece 20. In the bending piece set 24, the distal-most end bending piece 20 and the respective bending pieces 25 are connected to each other such that the pieces which are disposed adjacent to each other in the longitudinal direction are rotatable relative to each other by a pair of left and right pivotally supporting portions 26.

Wire guides 25a are formed on the predetermined bending pieces 25 which form the bending piece set 24, and any one of the respective towing wires 23 which pass through the insertion section 2 passes through each wire guide 25a. When each towing wire 23 is towed or slackened in response to an operation input by the operator to the operation section 3, the bending piece set 24 (bending portion 7) can be bent in the upward or downward direction.

In the bending piece set 24 having such a configuration, a signal cable 11c extending from the image pickup unit 11, the towing wires 23, the light guide, and the treatment instrument channel 12 pass through. An outer periphery of the bending piece set 24 is covered by a bending rubber 22.

The flexible tube portion 8 includes a helical tube 30 having flexibility which is passively bendable. A distal end side of the helical tube 30 is connected to a bending piece 25 positioned on a proximal-most end of the bending piece set 24.

In the helical tube 30, the signal cable 11c, the towing wires 23, the light guide, and the treatment instrument channel 12 described above pass through. An outer periphery of the helical tube 30 is covered by an outer skin 31.

As shown in FIG. 1, the operation section 3 includes a bend preventing portion 35, a grasping portion 36, and an operation section body 37.

The bend preventing portion 35 is connected to the flexible tube portion 8 in a state where the bend preventing portion 35 covers a proximal end of the flexible tube portion 8.

The grasping portion 36 is formed in a shape which allows a hand of an operator to grasp the grasping portion 36, and is continuously connected to a proximal end side of the bend preventing portion 35.

A treatment instrument insertion portion 38 is formed on a distal end side of the grasping portion 36. The treatment instrument insertion portion 38 has a treatment instrument insertion opening 38a through which various treatment instruments (not shown) are insertable. In the grasping portion 36, a proximal end side of the treatment instrument channel 12 communicates with the treatment instrument insertion opening 38a. A forceps plug (not shown) which is a lid member for closing the treatment instrument insertion opening 38a is detachably mounted on the treatment instrument insertion portion 38.

On a distal end side of the grasping portion 36, for example, at a position on a side opposite to the treatment instrument insertion portion 38, an operation unit 52 of a bending strength varying mechanism 50 described later (see FIG. 4) is disposed. The bending strength varying mechanism 50 is configured by making use of the treatment instrument channel 12, for example. The bending strength varying mechanism 50 can change a bending strength of the bending portion 7 between a first bending strength and a second bending strength. In such a case, the first bending strength is set to a bending strength which is suitable for insertion of the insertion section 2 into a normal lumen where neither a narrowed portion nor a meandering portion exists. The second bending strength is set to a bending strength higher (stronger) than the first bending strength.

The operation section body 37 is continuously connected to a proximal end side of the grasping portion 36. A bending lever 39 is mounted on the operation section body 37. The bending lever 39 bends the bending portion 7 in the upward or downward direction by towing or slackening the pair of towing wires 23.

In other words, for example, when the bending lever 39 is operated to be inclined toward a distal end side of the operation section 3, out of the pair of towing wires 23 which pass through the insertion section 2, one towing wire 23 positioned on an upper side is towed and, the other towing wire 23 positioned on a lower side is slackened so that the bending portion 7 is bent upward. On the other hand, when the bending lever 39 is operated to be inclined toward a proximal end side of the operation section 3, oat of the pair of towing wires 23 which pass through the insertion section 2, one towing wire 23 positioned on the upper side is slackened and, the other towing wire 23 positioned on the lower side is towed so that the bending portion 7 is bent downward.

A group of operation buttons 40 to which various functions of the endoscope 1 are allocated is mounted on the operation section body 37.

The universal cable 4 extends from a side portion of the operation section body 37. In the universal cable 4, various cables such as the signal cable 11c, the light guide and the like pass through.

An extending end of the universal cable 4 is connected to the connector 5, and the various cables and the light guide can be respectively connected to a video processor and a light source apparatus (neither shown) by the connector 5.

Next, the specific configuration of the bending strength varying mechanism 50 is described with reference to FIG. 2 to FIG. 4.

As shown in FIG. 2 to FIG. 4, the bending strength varying mechanism 50 includes: a coil spring 51 which forms a wire-like member; the operation unit 52 which applies an operation force for deforming the coil spring 51; and a closely wound coil 53 which forms a transmission member for transmitting an operation force applied to the operation unit 52 to the coil spring 51.

The coil spring 51 is helically wound around an outer periphery of the treatment instrument channel 12. A distal end 51a of the coil spring 51 is disposed in the distal end portion 6, and is fixed so as to be not movable with respect to the treatment instrument channel 12. The coil spring 51 in a region on a proximal end side with respect to the distal end 51a is mainly disposed at a position corresponding to the bending portion 7, and is movable with respect to the outer periphery of the treatment instrument channel 12. In other words, the coil spring 51 in the region on a proximal end side with respect to the distal end 51a is disposed having a slight gap with respect to the outer periphery of the treatment instrument channel 12. With such a configuration, the coil spring 51 is movable with respect to the outer periphery of the treatment instrument channel 12.

The coil spring 5 is disposed to assume a natural state where the coil spring 51 is not compressed substantially when the operation unit 52 is not operated. In the embodiment, a bending strength of the bending portion 7 in upward and downward directions is basically optimized by taking into account a bending strength of the coil spring 51 when the coil spring 51 is in a natural state in addition to bending strengths of the signal cable 11 c, the light guide, and various internal components in the treatment instrument channel 12. In other words, the bending strength of the bending portion 7 in the upward and downward directions when the coil spring 51 is in a natural state is set to, for example, a first bending strength which does not generate passive bending when the insertion section 2 is pushed mainly into a normal lumen having neither a narrowed portion nor a meandering portion while reducing an operation resistance in the bending lever 39 as much as possible.

The operation unit 52 has a slide guide 60 disposed in the grasping portion 36 (operation section 3). A guide hole 60a which extends in a longitudinal axis direction of the grasping portion 36 is formed in the slide guide 60, and the inside and the outside of the grasping portion 36 communicate with each other through the guide hole 60a.

The slide member 61 (axial-direction slide member) which forms an operation member is disposed outside the grasping portion 36. A key 62 which is slidable with respect to the guide hole 60a is formed on a back surface of the slide member 61 in a protruding manner, and a protruding end side of the key 62 protrudes into the grasping portion 36 through the guide hole 60a. With such a configuration, the slide member 61 is supported on the grasping portion 36, and is movable in an advancing and retracting manner in an axial direction that the guide hole 60a extends.

A channel insertion hole 62a which penetrates the key 62 in a longitudinal axis direction is formed in a portion of the key 62 on a protruding end side protruding toward the inside of the grasping portion 36. The treatment instrument channel 12 passes through the channel insertion hole 62a in a relatively movable state.

Further, a cylindrical connecting portion 62b to which a proximal end portion of the closely wound coil 53 is connected is formed on the key 62 coaxially with the channel insertion hole 62a.

The closely wound coil 53 is integrally formed with the coil spring 51 using the same material, for example, and the closely wound coil 53 is wound helically in the same direction as the coil spring 51 on the outer periphery of the treatment instrument channel 12.

The closely wound coil 53 is mainly disposed at a position corresponding to a range from the flexible tube portion 8 to a distal end side of the grasping portion 36, and is movable with respect to the outer periphery of the treatment instrument channel 12. In other words, the closely wound coil 53 is disposed having a slight gap with respect to the outer periphery of the treatment instrument channel 12 and hence, the closely wound coil 53 is movable with respect to the outer periphery of the treatment instrument channel 12.

A proximal end of the closely wound coil 53 is connected to the connecting portion 62b formed on the key 62 of the slide member 61 and hence, the closely wound coil 53 can transmit an operation force applied to the slide member 61 of the operation unit 52 to the coil spring 51.

As shown in FIG. 2, a length of the closely wound coil 53 is set to a length at which the key 62 of the slide member 61 is positioned on a proximal end side of the guide hole 60a when the coil spring 51 is in a natural state. In other words, the length of the closely wound coil 53 is set to a length at which the coil spring 51 is brought into a natural state when the key 62 is positioned on the proximal end side of the guide hole 60a. With such a configuration, the closely wound coil 53 can transmit an operation force generated when a user operates the slide member 61 toward a distal end side of the guide hole 60a to the coil spring 51. In other words, the closely wound coil 53 can transmit an operation force for deforming the coil spring 51 by compression to the coil spring 51 (see FIG. 3).

A bending strength of the coil spring 51 deformed by compression in this manner becomes higher than the bending strength of the coil spring 51 in a natural state. Accordingly, the bending strength varying mechanism 50 can change the bending strength of the bending portion 7 to the second bending strength higher than the first bending strength.

In inserting the insertion section 2 of the endoscope 1 having such a configuration into a lumen of a subject, an operator, basically, in a state where a bending strength of the bending portion 7 is held at the first bending strength, grasps the grasping portion 36 by one hand and pushes the insertion section 2 into the subject by grasping the flexible tube portion 1 by the other hand.

In such an insertion operation, when the operator finds a narrowed portion or a meandering portion in front of the insertion section 2 in the lumen, the operator operates the slide member 61 of the operation unit 52 by the hand which grasps the operation section 3, and pushes the insertion section 2 into the subject by grasping the flexible tube portion 8 by the other hand in a state where the bending strength of the bending portion 7 is changed over to the second bending strength. Accordingly, even when the insertion section 2 is pushed into the lumen, the passive bending of the bending portion 7 is suppressed. Accordingly, a pushing force generated by the user is accurately transmitted to the distal end portion 6, and it is possible to allow the distal end portion 6 (insertion section 2) to pass through the narrowed portion or the meandering portion.

According to the embodiment, the bending strength varying mechanism 50 includes: the coil spring 51 which is helically wound around the outer periphery of the treatment instrument channel 12 disposed in the insertion section 2, and the distal end of which is fixed to the treatment instrument channel 12 on a distal end portion 6 side with respect to the bending portion 7; and the slide member 61 which is disposed on the proximal end side of the coil spring 51, and applies an operation force for deforming the coil spring 51 such that a bending strength of at least a portion of the coil spring 51 which corresponds to the inside of the bending portion 7 is increased. With such a configuration, the insertion section 2 can ensure favorable insertability even when a portion which makes the insertion of the insertion section 2 difficult such as a narrowed portion or a meandering portion exists in the subject.

In other words, as described previously, in a normal operation time where neither a narrowed portion nor a meandering portion exists in front of the insertion section 2 in a lumen, the insertion of the insertion section 2 is performed by setting the bending strength of the bending portion 7 to the first bending strength. In a case where a narrowed portion or a meandering portion exists, the bending strength of the bending portion 7 is increased to the second bending strength. Accordingly, it is possible to realize favorable insertability even when a narrowed portion or a meandering portion exists while ensuring operability or the like of a bending operation during a normal operation time.

In this case, the bending strength varying mechanism 50 is configured by making use of the existing annular member such as the treatment instrument channel 12 and hence, it is possible to prevent the structure of the bending strength varying mechanism 50 from becoming complicated, and it is also possible to prevent the increase of a diameter of the insertion section 2.

The transmission member which transmits an operation force applied to the slide member 61 to the coil spring 51 is formed of the closely wound coil 53 which is integrally formed with the coil spring 51 using the same material as the coil spring 51 and hence, the configuration of the bending strength varying mechanism 50 can be further simplified.

Figure 5:
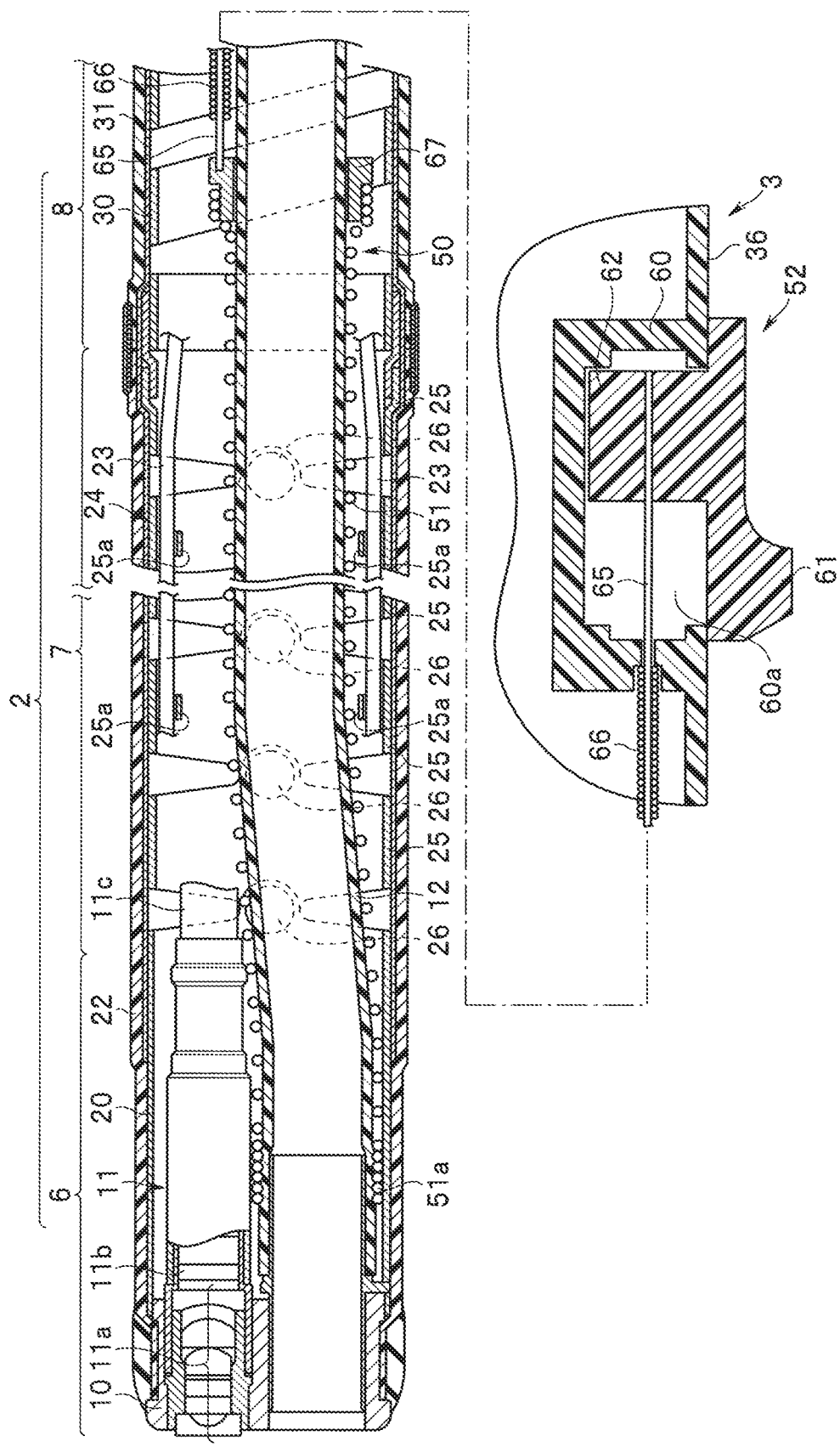
FIG. 5 is a view showing a first modification of the first embodiment, and is a cross-sectional view of a main part of an insertion section and an operation section in a state where a bending portion has a first bending strength.
Figure 6:
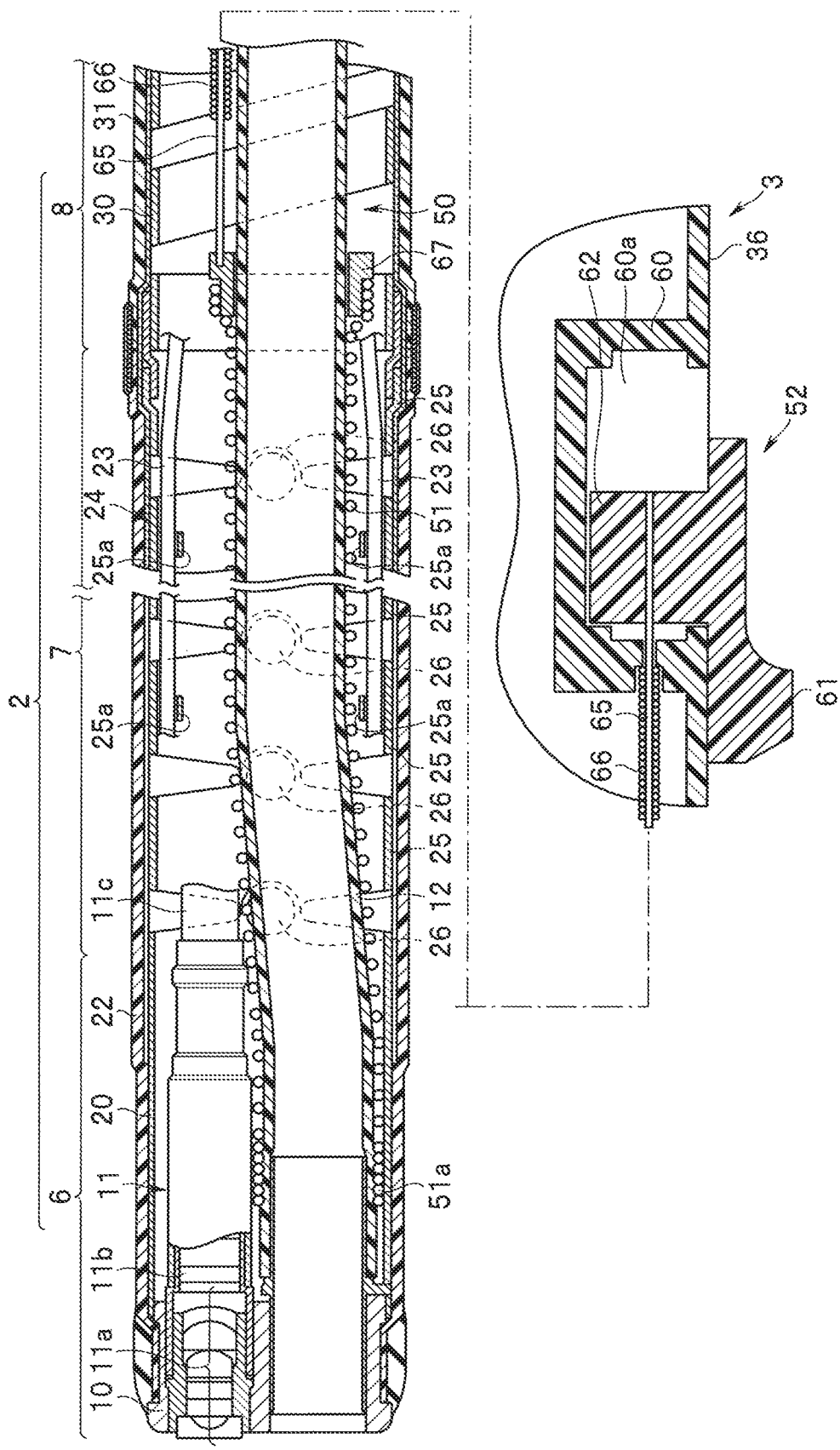
FIG. 6 is a cross-sectional view of a main part of the insertion section and the operation section in a state where a bending strength of the bending portion is a second bending strength higher than the first bending strength in the first modification.

For example, as shown in FIGS. 5 and 6, in the bending strength varying mechanism 50 of the embodiment, as the transmission portion which transmits an operation force applied to the slide member 61 to the coil spring 51, an operation wire 65 may be adopted in place of the closely wound coil 53.

In this case, for example, as shown in FIGS. 5 and 6, the operation wire 65 is disposed in the insertion section 2 along the treatment instrument channel 12 in a state where the operation wire 65 passes through a closely wound coil 66 or the like for preventing buckling or the like.

To uniformly transmit an operation force applied to the slide member 61 to a proximal end of the coil spring 51, for example, a proximal end of the coil spring 51 and a distal end of the operation wire 65 are connected to a ring-shaped connecting member 67 which is movable on an outer periphery of the treatment instrument channel 12.

A proximal end of the operation wire 65 is directly connected to the key 62 in a state where the proximal end of the operation wire 65 is spaced apart from the treatment instrument channel 12.

Figure 7:
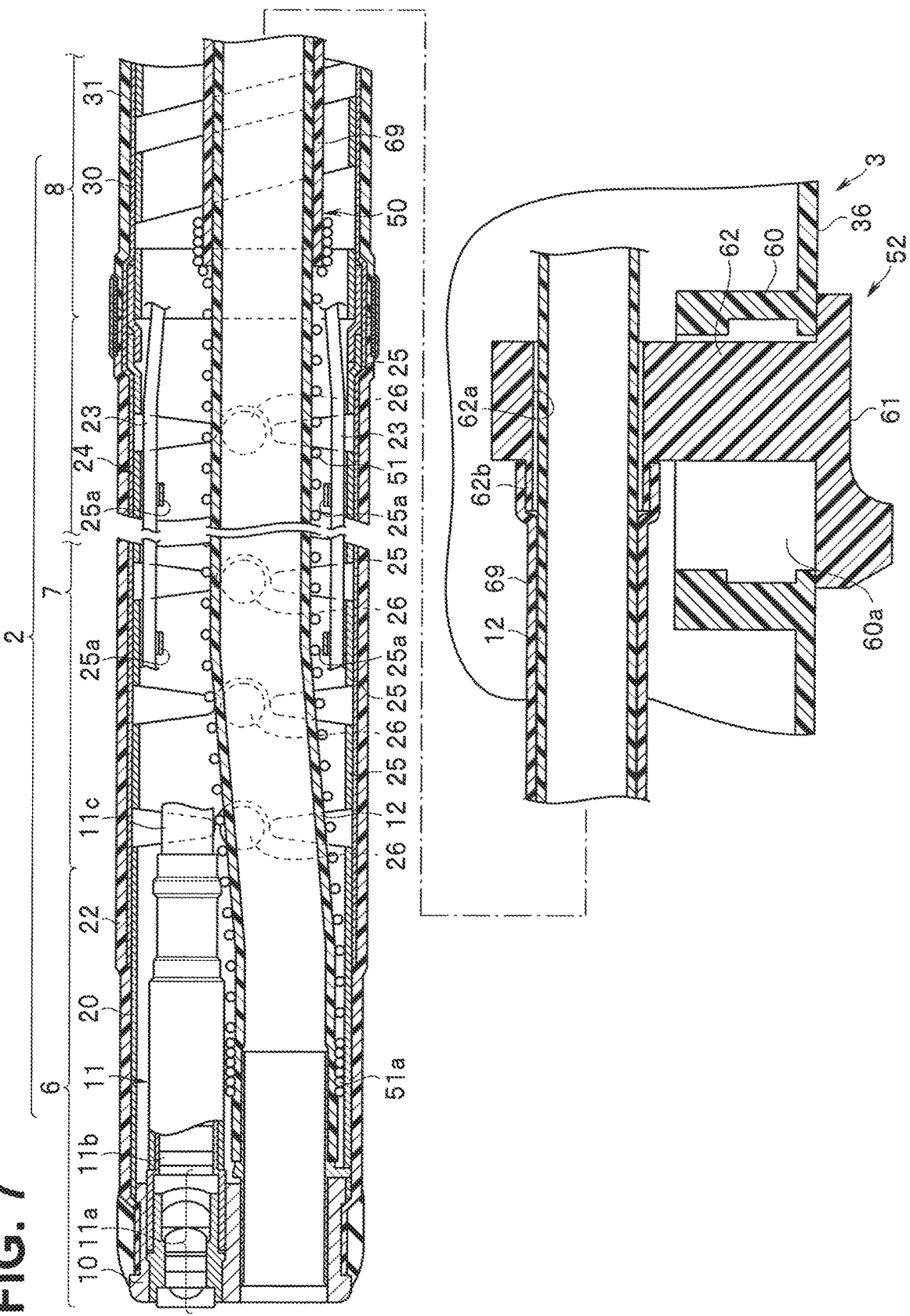
FIG. 7 is a view showing a second modification of the first embodiment, and is a cross-sectional view of a main part of an insertion section and an operation section in a state where a bending portion has a first bending strength.
Figure 8:
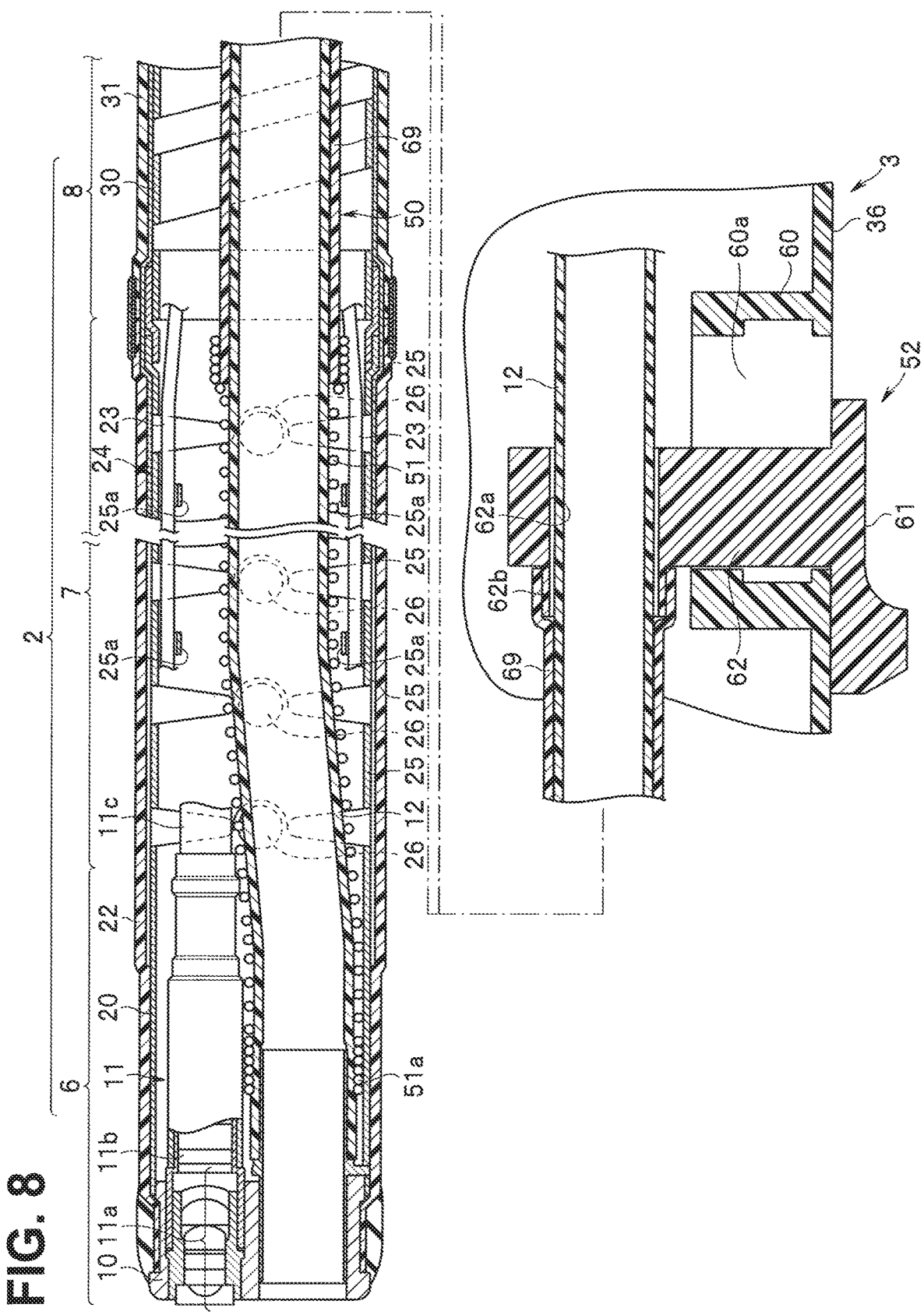
FIG. 8 is a cross-sectional view of a main part of the insertion section and the operation section in a state where a bending strength of the bending portion is a second bending strength higher than the first bending strength in the second modification.

For example, as shown in FIGS. 7 and 8, in the bending strength varying mechanism 50 of the embodiment, as a transmitting portion for transmitting an operation force applied to the slide member 61 to the coil spring 51, a tube 69 which is disposed so as to movably cover the outer periphery of the treatment instrument channel 12 can be adopted in place of the closely wound coil 53.

In this case, a proximal end of the coil spring 51 is fixed to an outer periphery of a distal end of the tube 69, for example. A proximal end of the tube 69 is connected to a connecting portion 62b formed on the key 62.

Figure 9:
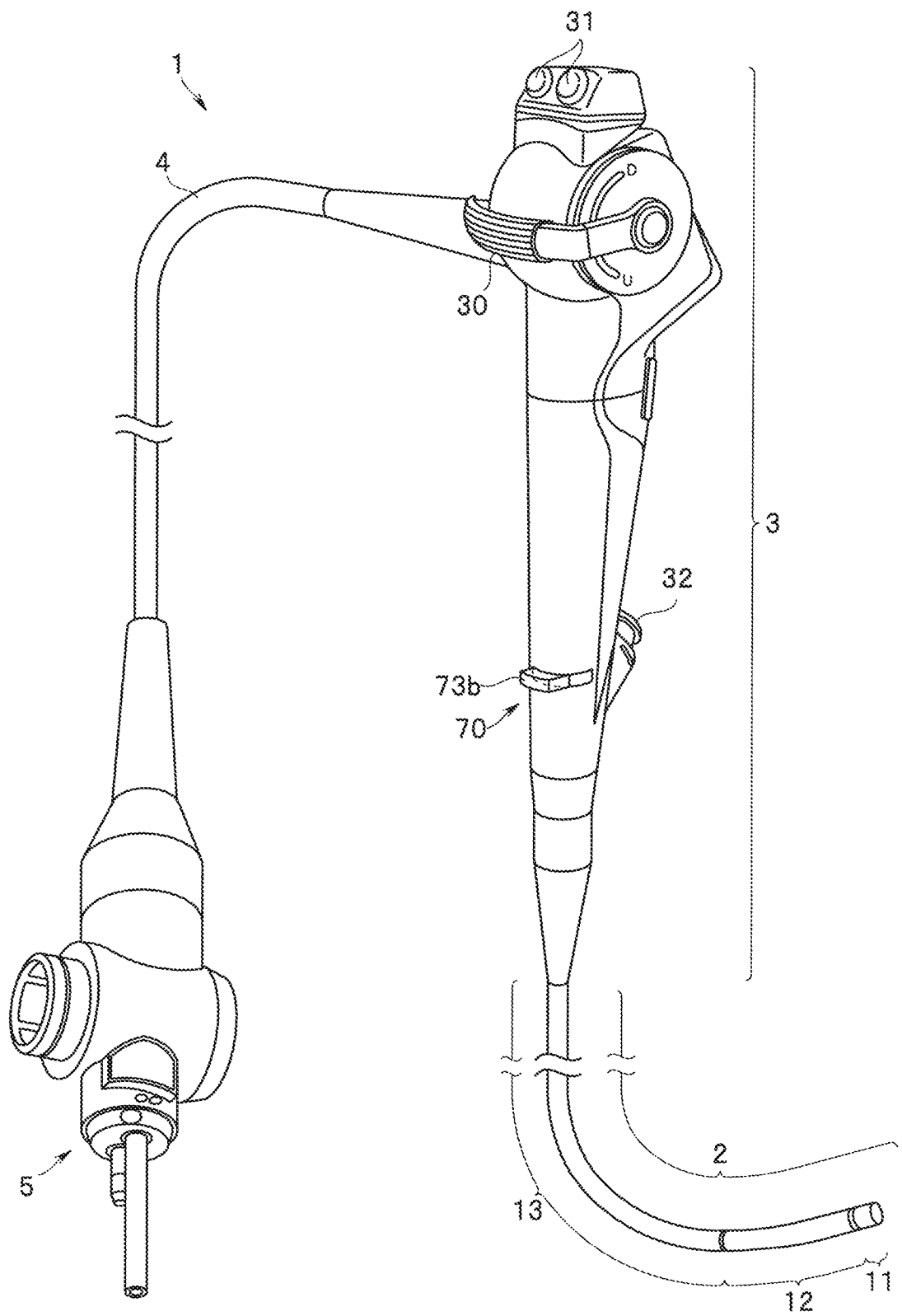
FIG. 9 is a perspective view showing an external appearance of an endoscope according to a second embodiment.
Figure 10:
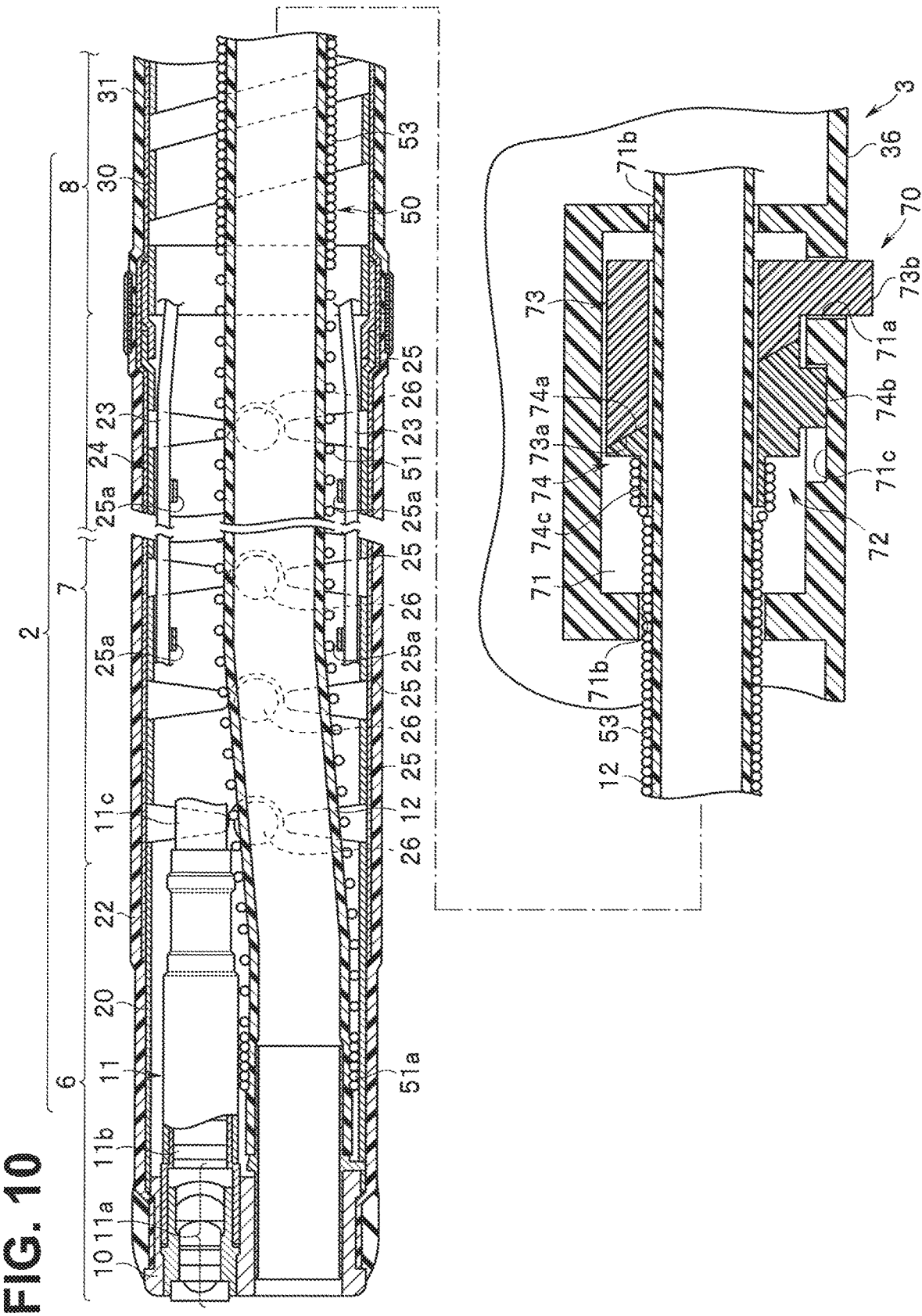
FIG. 10 is a cross-sectional view of a main part of an insertion section and an operation section in a state where a bending portion has a first bending strength in the second embodiment.
Figure 11:
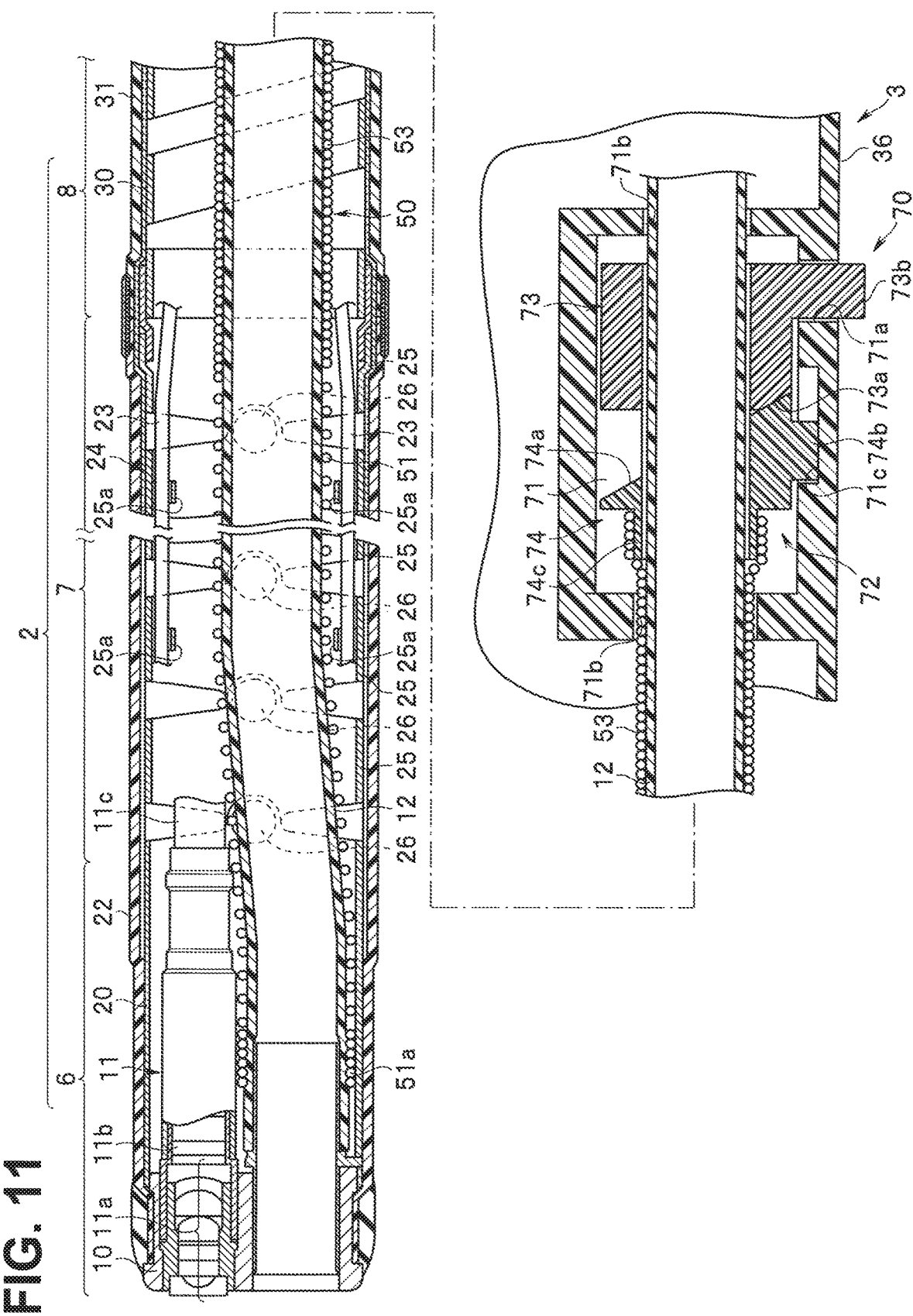
FIG. 11 is a cross-sectional view of a main part of the insertion section and the operation section in a state where a bending strength of the bending portion is a second bending strength higher than the first bending strength in the second embodiment.
Figure 12:
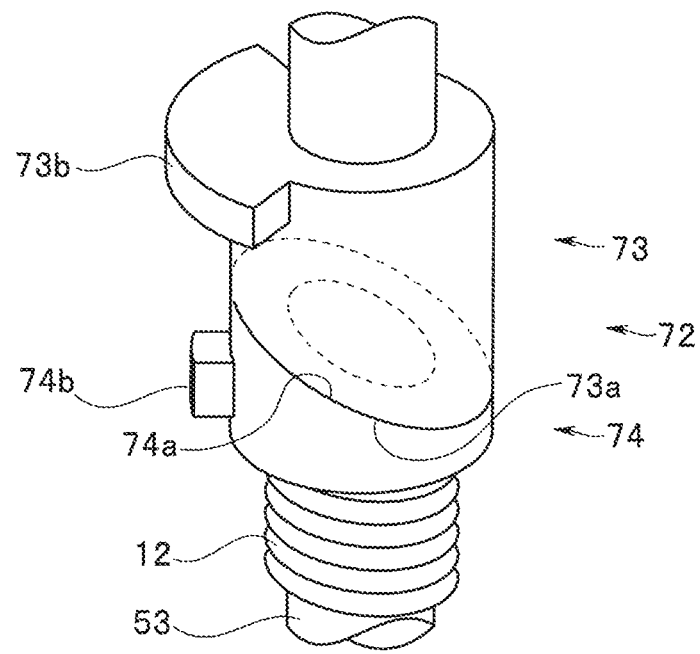
FIG. 12 is a perspective view showing a main part of a cam mechanism in a state where an operation lever is not operated in the second embodiment.
Figure 13:
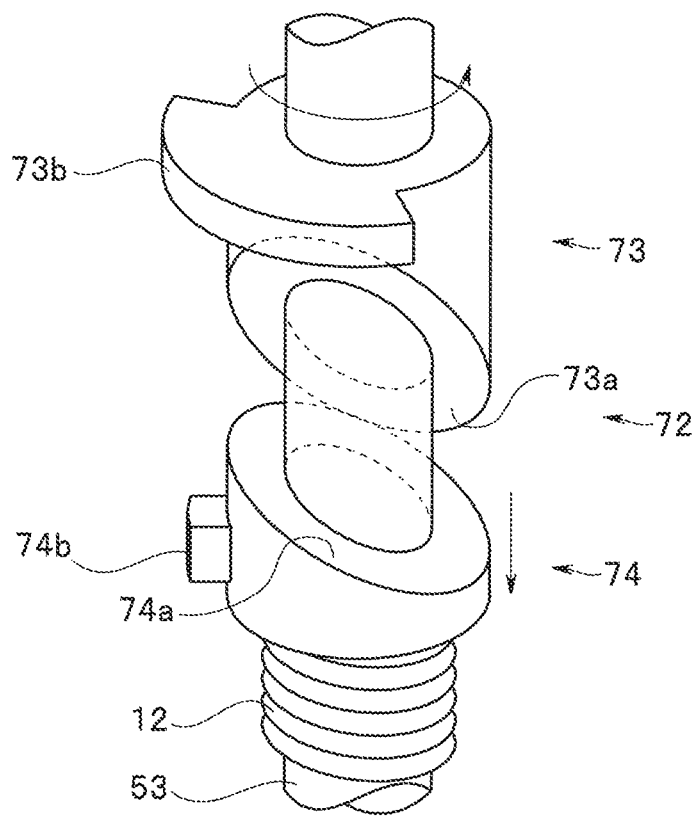
FIG. 13 is a perspective view showing a main part of the cam mechanism in a state where the operation lever is operated in the second embodiment.

Next, FIG. 9 to FIG. 13 relate to a second embodiment of the present invention. FIG. 9 is a perspective view showing an external appearance of an endoscope, FIG. 10 is a cross-sectional view of a main part of an insertion section and an operation section in a state where a bending portion has a first bending strength, FIG. 11 is a cross-sectional view of a main part of the insertion section and the operation section in a state where a bending strength of the bending portion is a second bending strength higher than the first bending strength, FIG. 12 is a perspective view showing a main part of a cam mechanism in a state where an operation lever is not operated, and FIG. 13 is a perspective view showing a main part of the cam mechanism in a state where the operation lever is operated.

The second embodiment differs from the above-mentioned first embodiment mainly with respect to a configuration of an operation unit of a bending strength varying mechanism 50. Accordingly, the description of components substantially equivalent to the corresponding components of the above-mentioned first embodiment is suitably omitted by affixing the same symbols.

As shown in FIG. 10 and FIG. 11, an operation unit 70 of the embodiment has a cam chamber 71 formed in a grasping portion 36 (operation section 3). A communication hole 7th which extends in a direction perpendicular to a longitudinal axis of the grasping portion 36 is formed in the cam chamber 71, and the inside of the cam chamber 71 communicates with the outside of the grasping portion 36 through the communication hole 71a.

A channel through hole 71b which allows a treatment instrument channel 12 to pass through the cam chamber 71 is formed in a wall portion of the cam chamber 71 on a distal end side and a wall portion of the cam chamber 71 on a proximal end side.

A guide groove 71c which extends in a longitudinal axis direction of the grasping portion 36 is formed in the cam chamber 71.

The treatment instrument channel 12 which passes through the communication hole 71a passes through the inside of the cam chamber 71, and a driver 73 and a follower 74 which form a cam mechanism 72 are housed in the cam chamber 71.

The driver 73 is formed of a member having an approximately cylindrical shape, and is pivotally supported on an outer periphery of the treatment instrument channel 12.

A distal end surface 73a of the driver 73 is formed as a first cam surface inclined with respect to a longitudinal axis of the grasping portion 36.

An operation lever 73b is formed on a side portion of the driver 73 in a protruding manner. The operation lever 73b is inserted into the communication hole 71a, and a protruding end portion of the operation lever 73b protrudes to the outside of the grasping portion 36 as an operation member (more specifically, a circumferentially rotating member) (see FIG. 9 to FIG. 11). With such a configuration, a movement of the driver 73 in the longitudinal axis direction of the grasping portion 36 is prohibited, and only a rotation of the driver 73 in the circumferential direction about the longitudinal axis of the grasping portion 36 is allowed.

The follower 74 is formed of a member having an approximately cylindrical shape, and is pivotally supported on the outer periphery of the treatment instrument channel 12 on a distal end side with respect to the driver 73.

A proximal end surface 74a of the follower 74 is formed as a second cam surface inclined with respect to the longitudinal axis of the grasping portion 36.

A key 74b is formed on a side portion of the follower 74 in a protruding manner, and the key 74b engages with the guide groove 71c. With such a configuration, a rotation of the follower 74 in the circumferential direction about the longitudinal axis of the grasping portion 36 is prohibited, and only a movement of the follower 74 in the longitudinal axis direction is allowed.

A connecting member 74c to which a proximal end portion of a closely wound coil 53 is connected is formed on a distal end of the follower 74.

The driver 73 and the follower 74 which are disposed in the cam chamber 71 are set such that, when the driver 73 is positioned on one rotary end defined by the communication hole 71a, the distal end surface 73a of the driver 73 and the proximal end surface 74a of the follower 74 are brought into face contact with each other so that the follower 74 is positioned on a proximal end side defined by the guide groove 71c (see FIG. 10, FIG. 12). The driver 73 and the follower 74 are also set such that, when the driver 73 is rotated to the other rotary end side defined by the communication hole 71a, the contact position between the distal end surface 73a of the driver 73 and the proximal end surface 74a of the follower 74 changes so that the follower 74 moves toward the distal end side defined by the guide groove 71c (see FIGS. 11 and 13).

A length of the closely wound coil 53 is set at a length at which the operation lever 73b is positioned on one rotary end of the communication hole 71a when the coil spring 51 is in a natural state (see FIG. 10). Accordingly, the closely wound coil 53 can transmit an operation force generated when a user operates the operation lever 73b from one rotary end of the communication hole 71a to the other rotary end of the communication hole 71a to the coil spring 51. More specifically, an operation force generated when the user rotatably operates the operation lever 73b is convened into an operation force in an axial direction in the cam mechanism 72 and, thereafter, the operation force is transmitted to the coil spring 51 by the closely wound coil 53 whereby the coil spring 51 is deformed by compression. Accordingly, a bending strength of the bending portion 7 is changed over from a first bending strength to a second bending strength.

The embodiment having such a configuration can acquire substantially the same manner of operation and advantageous effects as the above-mentioned first embodiment.

Figure 14:
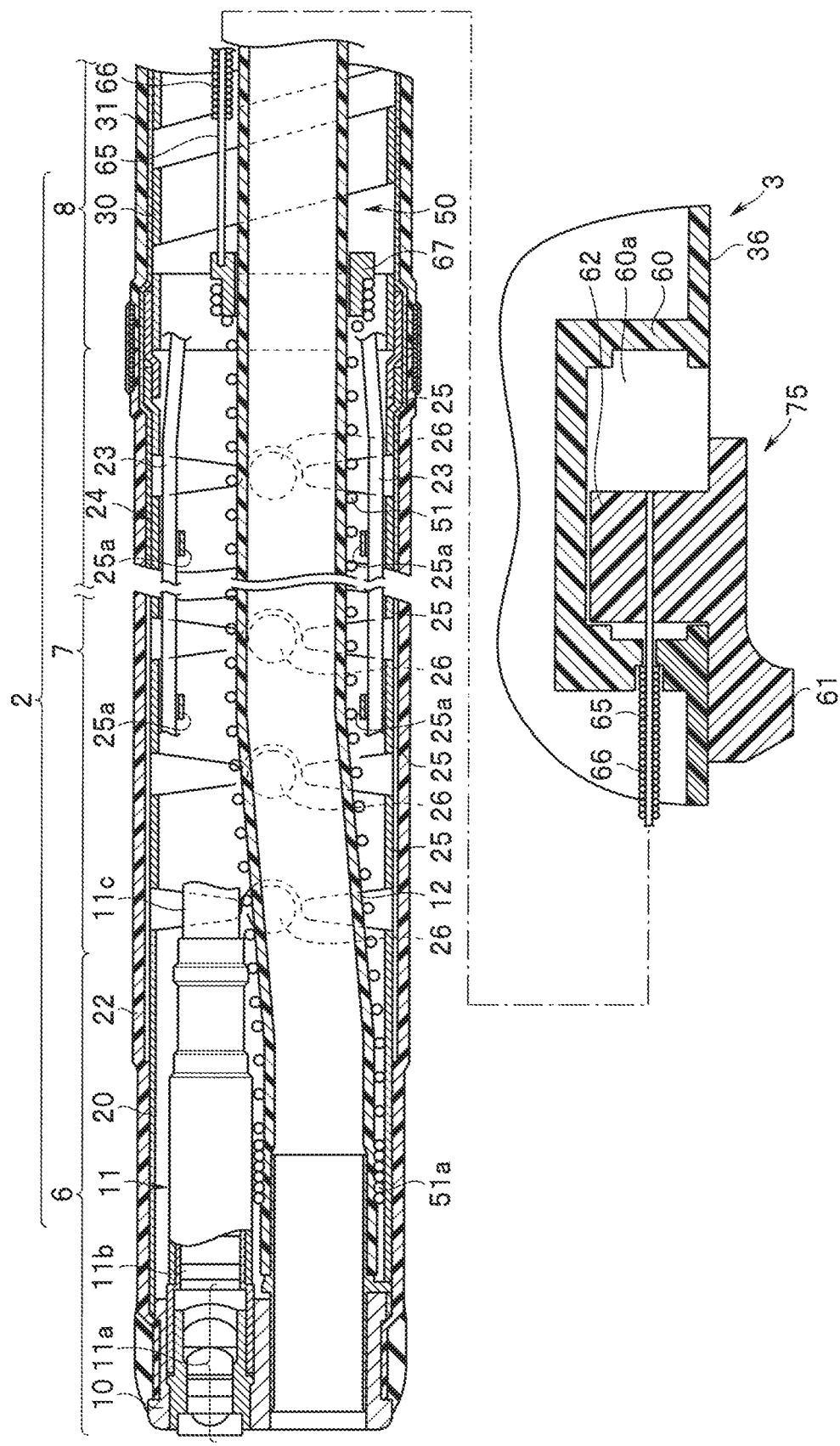
FIG. 14 is a view showing a third embodiment, and is a cross-sectional view of a main part of an insertion section and an operation section in a state where a bending portion has a first bending strength.
Figure 15:
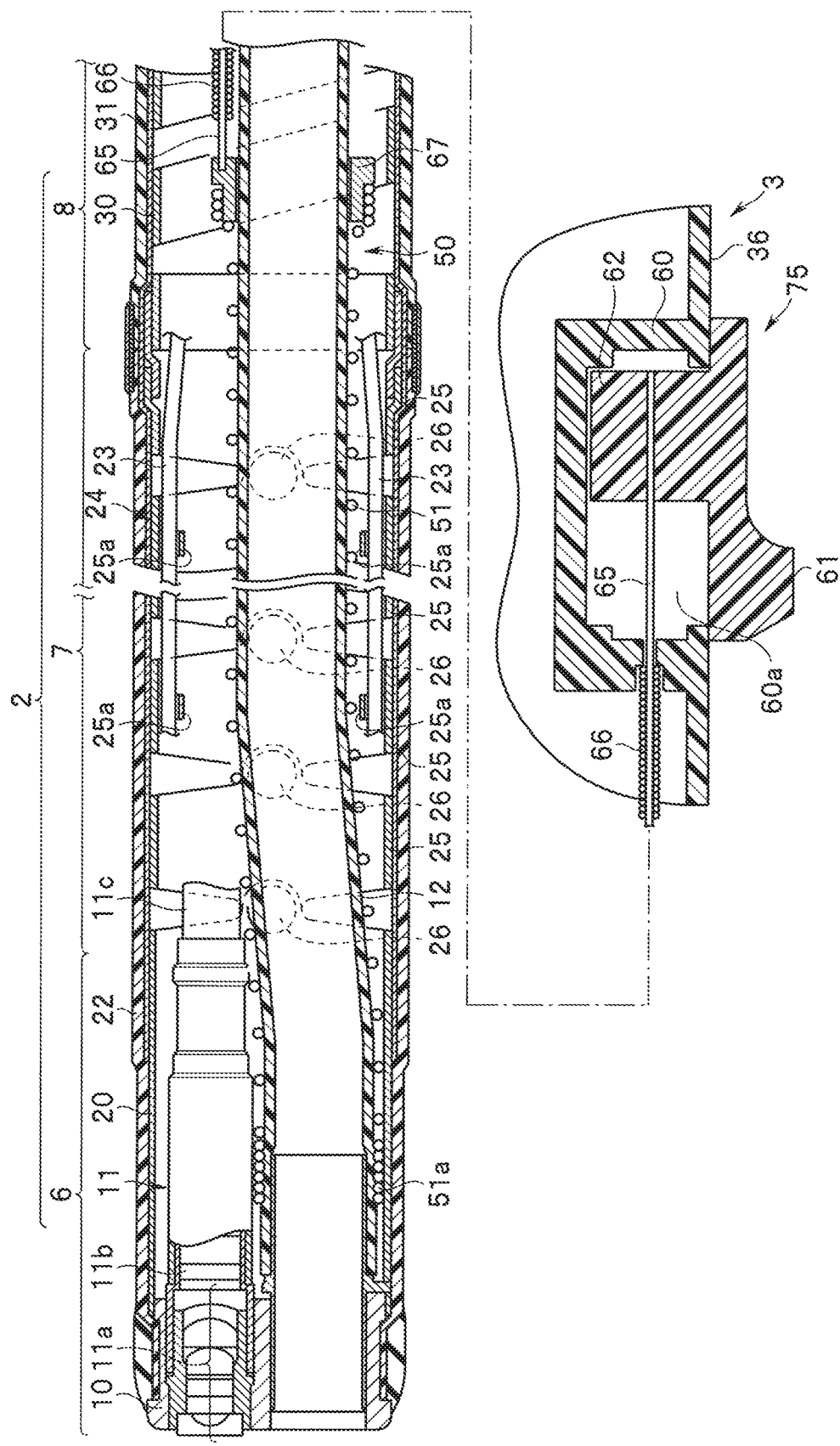
FIG. 15 is a cross-sectional view of a main part of the insertion section and the operation section in a state where a bending strength of the bending portion is a second bending strength higher than the first bending strength in the third embodiment.

FIG. 14 and FIG. 15 relate to a third embodiment of the present invention. FIG. 14 is a cross-sectional view of a main part of an insertion section and an operation section in a state where a bending portion has a first bending strength, and FIG. 15 is a cross-sectional view of a main part of the insertion section and the operation section in a state where a bending strength of the bending portion is a second bending strength higher than the first bending strength.

In the first embodiment described above, the description has been made with respect to the configuration where a bending strength of the bending portion 7 is changed over from a first bending strength to a second bending strength by changing the coil spring 51 from a natural state to a compressed state. The present embodiment differs from the first embodiment mainly with respect to a point that a bending strength of the bending portion 7 is changed over from a first bending strength to a second bending strength by tightening a treatment instrument channel 12 by changing a coil spring 51 from a natural state to an extended state. Accordingly, the description of components substantially equivalent to the corresponding components of the above-mentioned first embodiment is suitably omitted.

As shown in FIG. 14 and FIG. 15, in the embodiment, an operation unit 75 of a bending strength varying mechanism 50 includes an operation wire 65 as a transmitting portion for transmitting an operation three applied to a slide member 61 to a coil spring 51.

The operation wire 65 is disposed in the insertion section 2 in a state where the operation wire 65 passes through a closely wound coil 66 or the like for preventing buckling of the operation wire 65.

To uniformly transmit an operation force applied to the slide member 61 to a proximal end of the coil spring 51, for example, the proximal end of the coil spring 51 and a distal end of the operation wire 65 are connected to a ring-shaped connecting member 67 which is movable on an outer periphery of a treatment instrument channel 12.

A proximal end of the operation wire 65 is directly connected to a key 62 independently from a treatment instrument channel 12.

A length of the operation wire 65 is set to a length at which a key 62 of the slide member 61 is positioned on a distal end side of a guide hole 60a When the coil spring 51 is in a natural state (see FIG. 14). With such a configuration, the operation wire 65 can transmit an operation force generated when user operates the slide member 61 to a proximal end side of a guide hole 60a to the coil spring 51. In other words, the operation wire 65 can transmit an operation force for moving (deforming) the coil spring 51 in an extending direction to the coil spring 51 (see FIG. 15).

When the coil spring 51 is extended and deformed in this manner, the coil spring 51 is strongly wound around an outer periphery of the treatment instrument channel 12 and tightens the treatment instrument channel 12 thus making the relative movement between the coil spring 51 and the treatment instrument channel 12 impossible. Accordingly, the bending strength of the coil spring 51 extended and deformed (and the treatment instrument channel 12) is set higher than the bending strength in a natural state. As a result, a bending strength of the bending portion 7 is changed over to a second bending strength higher than a first bending strength.

The present embodiment having such a configuration can acquire substantially the same advantageous effects as the above-mentioned first embodiment.

Figure 16:
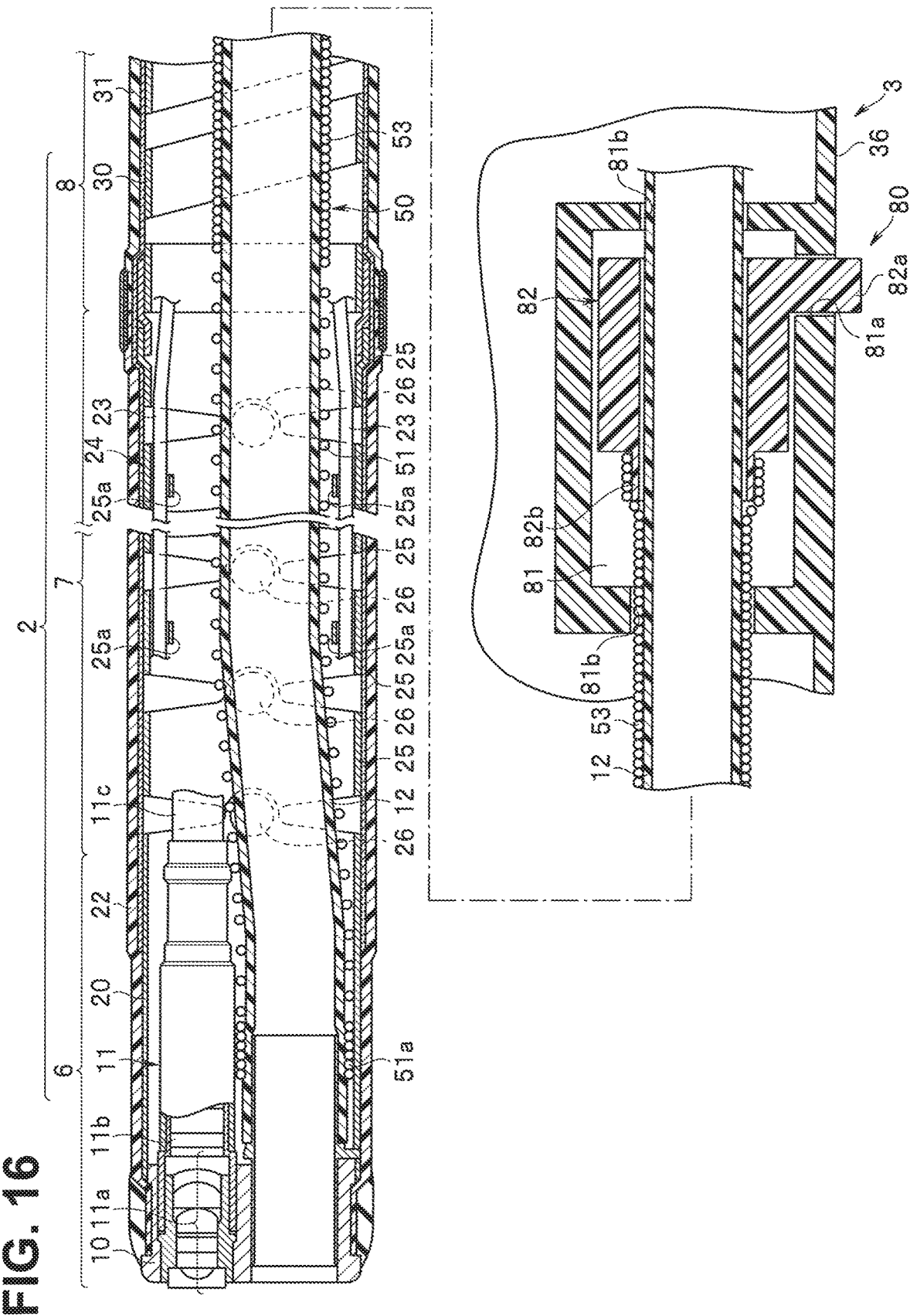
FIG. 16 is a view showing a fourth embodiment, and is a cross-sectional view of a main part of an insertion section and an operation section.

Next, FIG. 16 relates to a fourth embodiment of the present invention. FIG. 16 is a cross-sectional view of a main part of an insertion section and an operation section.

The fourth embodiment differs from the above-mentioned first embodiment mainly with respect to the configuration of an operation unit of a bending strength varying mechanism 50. Accordingly, the description of components substantially equivalent to the corresponding components of the above-mentioned first embodiment is suitably omitted by affixing the same symbols.

As shown in FIG. 16, in the present embodiment, an operation unit 80 has a housing chamber 81 formed in a grasping portion 36 (operation section 3). A communication hole 81a which extends in a direction perpendicular to a longitudinal axis of the grasping portion 36 is formed in the housing chamber 81, and the inside of the housing chamber 81 communicates with the outside of the grasping portion 36 through the communication hole 81a.

A channel insertion hole 81b which allows a treatment instrument channel 12 to pass through the housing chamber 81 is formed in a wall portion of the housing chamber 81 on a distal end side and a wall portion of the housing chamber 81 on a proximal end side.

The treatment instrument channel 12 which passes through the channel insertion holes 81b passes through the inside of the housing chamber 81, and a sleeve member 82 is pivotally supported on the treatment instrument channel 12.

An operation lever 82a is formed on a side portion of the sleeve member 82 in a protruding manner. The operation lever 82a is inserted into the communication hole 81a, and a protruding end portion of the operation lever 82a protrudes toward the outside of the grasping portion 36 which forms an operation member (more specifically, a circumferentially rotating member). With such a configuration, the movement of the sleeve member 82 in a longitudinal axis direction of the grasping portion 36 is prohibited, and only the rotation of the sleeve member 82 in the circumferential direction about the longitudinal axis of the grasping portion 36 is allowed.

A connecting member 82b to which a proximal end portion of a closely wound coil 53 is connected is formed on a distal end of the sleeve member 82.

A proximal end of the closely wound coil 53 is connected to the connecting member 82b such that the coil spring 51 is brought into a natural state when the operation lever 82a is positioned at one end side of the communication hole 81a. With such a configuration, the closely wound coil 53 can transmit an operation force generated when a user operates the operation lever 82a from one end side to the other end side of the communication hole 81a. A direction of the operation force is set so as to agree with a winding direction of the coil spring 51 and the closely wound coil 53. Accordingly, a bending strength of the bending portion 7 can be changed over from a first bending strength to a second bending strength.

In other words, when an operation force in the winding direction is transmitted, the coil spring 51 moves with respect to an outer periphery of the treatment instrument channel 12 in a strongly winding manner thus tightening the treatment instrument channel 12 and hence, the relative movement between the coil spring 51 and the treatment instrument channel 12 is not possible. Accordingly, a bending strength of the coil spring 51 (and the treatment instrument channel 12) deformed in a winding direction becomes higher than the bending strength when the coil spring 51 is in a natural state. As a result, the bending strength of the bending portion 7 is changed over to the second bending strength higher than the first bending strength.

The embodiment can acquire substantially the same manner of operation and advantageous effects as the above-mentioned first embodiment.

Figure 17:
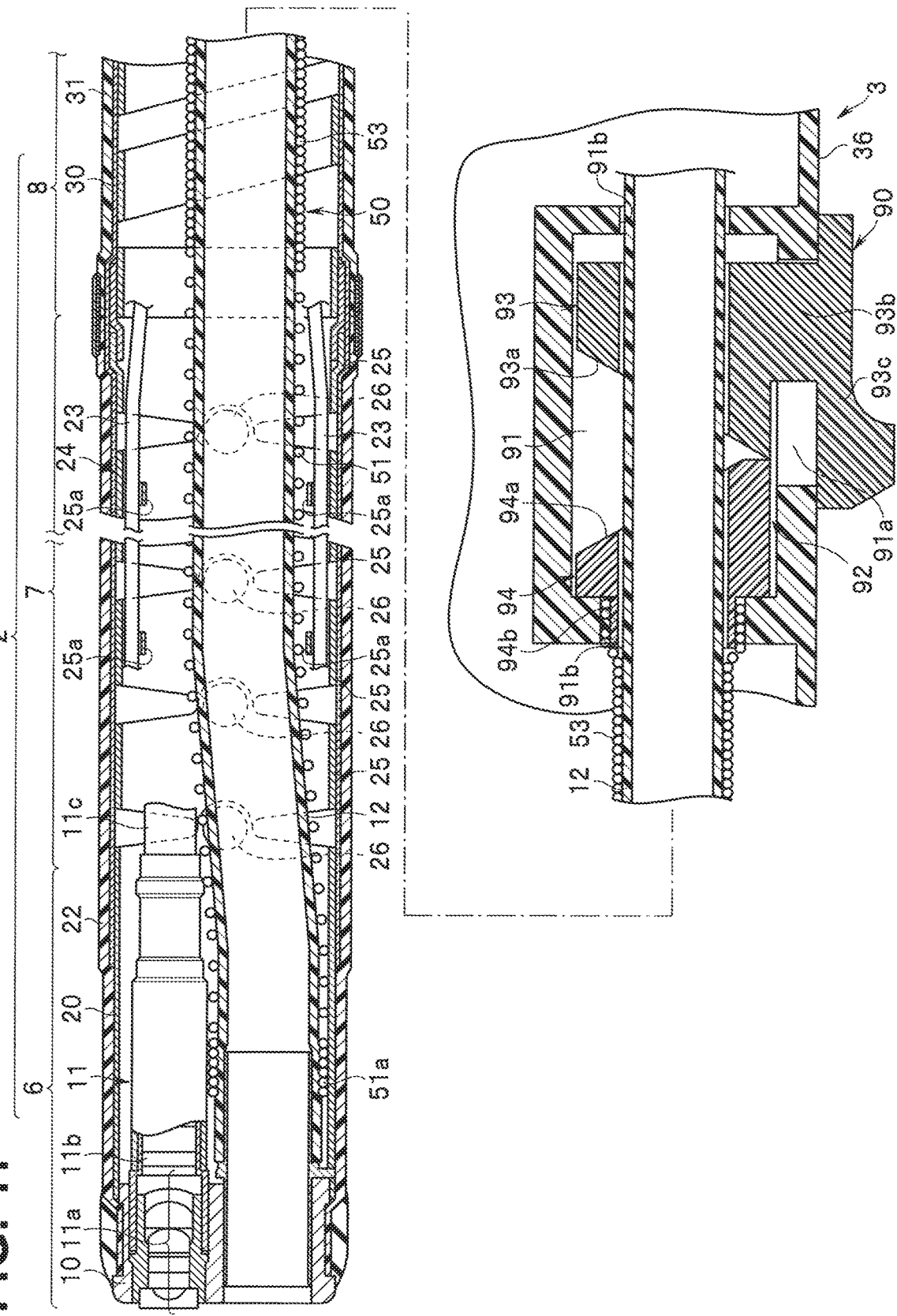
FIG. 17 is a view showing a fifth embodiment, and is a cross-sectional view of a main part of an insertion section and an operation section in a state where a bending portion has a first bending strength.
Figure 18:
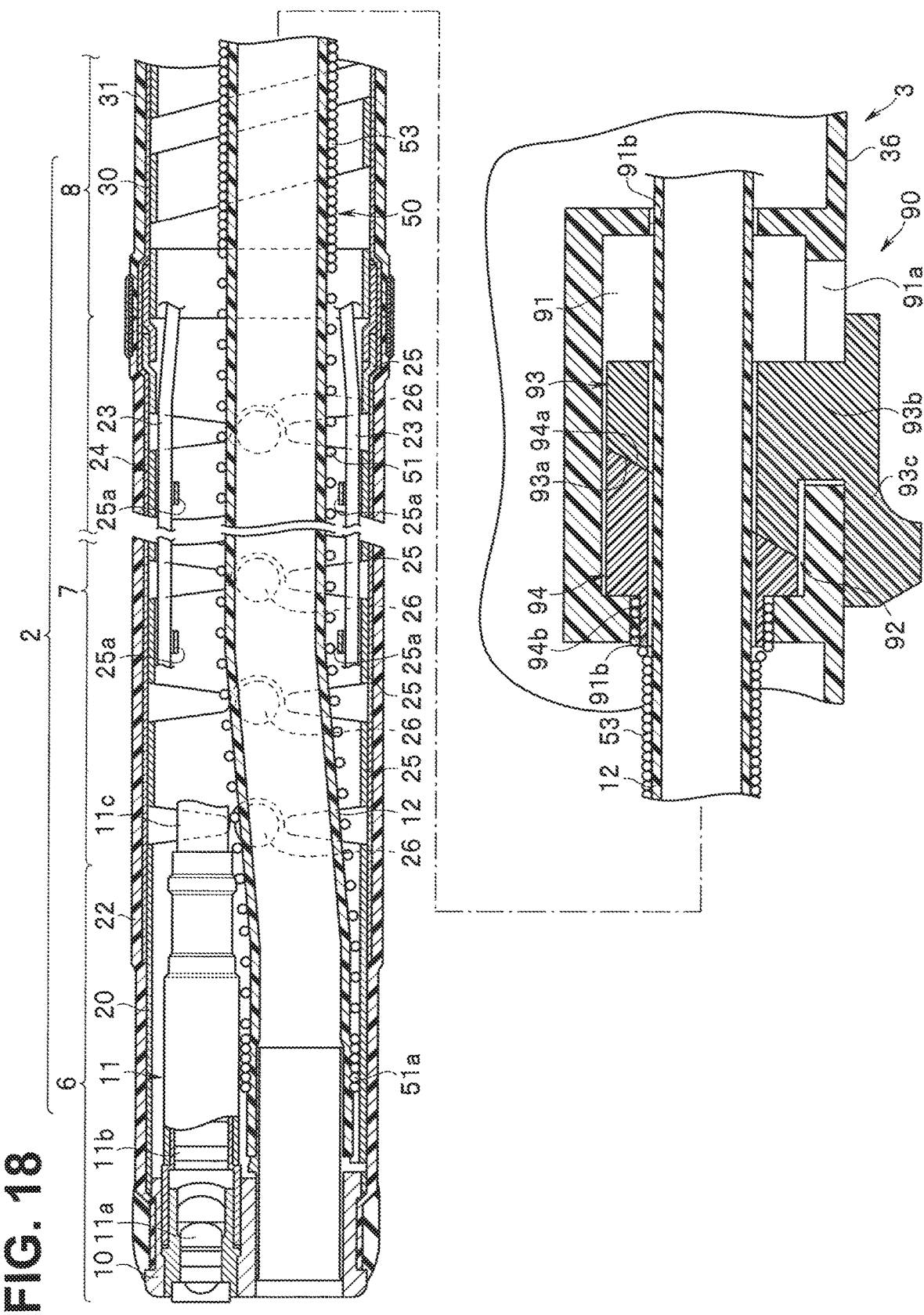
FIG. 18 is a cross-sectional view of a main part of the insertion section and the operation section in a state where a bending strength of the bending portion is a second bending strength higher than the first bending strength in the fifth embodiment.
Figure 19:
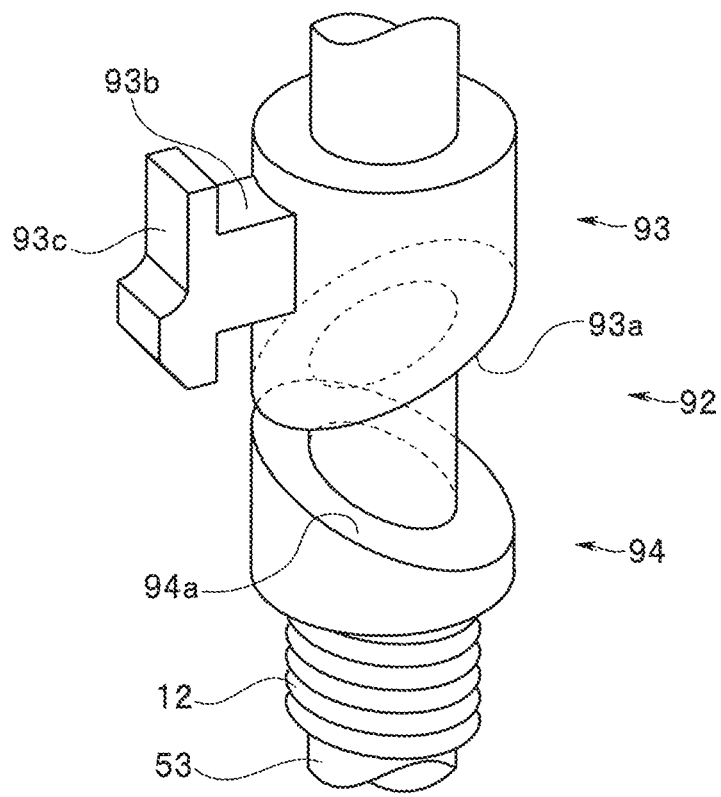
FIG. 19 is a perspective view showing a main part of a cam mechanism in a state where a slide member is not operated in the fifth embodiment.
Figure 20:
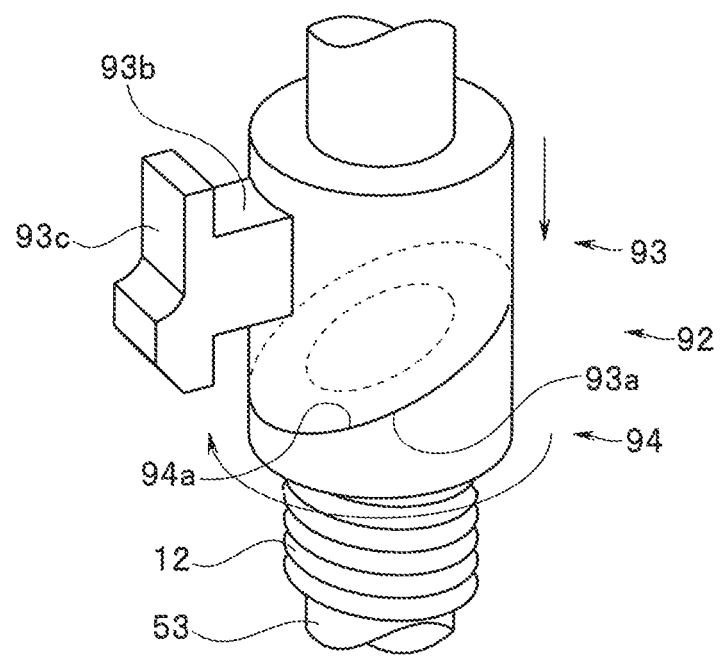
FIG. 20 is a perspective view showing a main part of the cam mechanism in a state where the slide member is operated in the fifth embodiment.

Next, FIG. 17 to FIG. 20 relate to a fifth embodiment of the present invention. FIG. 17 is a cross-sectional view of a main part of an insertion section and an operation section in a state where a bending portion has a first bending strength, FIG. 18 is a cross-sectional view of a main part of the insertion section and the operation section in a state where a bending strength of the bending portion is a second bending strength higher than the first bending strength, FIG. 19 is a perspective view showing a main part of a cam mechanism in a state where a slide member is not operated, and FIG. 20 is a perspective view showing a main part of the cam mechanism in a state where the slide member is operated.

The fifth embodiment differs from the above-mentioned first embodiment mainly with respect to the configuration of an operation unit of a bending strength varying mechanism 50. Accordingly, the description of components substantially equivalent to the corresponding components of the above-mentioned first embodiment is suitably omitted by affixing the same symbols.

As shown in FIG. 17 and FIG. 18, an operation unit 90 of the embodiment has a cam chamber 91 disposed in a grasping portion 36 (operation section 3). A communication hole 91a which extends in a longitudinal axis direction of the grasping portion 36 is formed in the cam chamber 91, and the inside of the cam chamber 91 communicates with the outside of the grasping portion 36 through the communication hole 91a.

A channel insertion hole 91b which allows a treatment instrument channel 12 to pass through the cam chamber 91 is formed in a wall portion of the cam chamber 91 on a distal end side and a wall portion of the cam chamber 91 on a proximal end side.

The treatment instrument channel 12 passes through the inside of the cam chamber 91, and a driver 93 and a follower 94 which form a cam mechanism 92 are housed in the earn chamber 91.

The driver 93 is formed of a member having an approximately cylindrical shape, and is pivotally supported on an outer periphery of the treatment instrument channel 12.

A distal end surface 93a of the driver 93 is formed as a first cam surface inclined with respect to a longitudinal axis of the grasping portion 36.

A key 93 is formed on a side portion of the driver 93 in a protruding manner. The key 93b is inserted into the communication hole 90a. With such a configuration, a rotation of the driver 93 in the circumferential direction about the longitudinal axis of the grasping portion 36 is prohibited, and only a movement of the driver 93 in the longitudinal axis direction is allowed.

Outside the grasping portion 36, a slide member 93c which forms an operation member (axial-direction slide member) provided for moving the driver 93 in a longitudinal direction is fixed to a protruding end portion of the key 93b (see FIG. 17, 18).

The follower 94 is formed of a member having an approximately cylindrical shape, and is pivotally supported on an outer periphery of the treatment instrument channel 12 on a distal end side with respect to the driver 93.

A proximal end surface 94a of the follower 94 is formed as a second cam surface inclined with respect to the longitudinal axis of the grasping portion 36.

A connecting member 94b to which a proximal end portion of a closely wound coil 53 is connected is formed on a distal end of the follower 94.

A distal end surface of the follower 94 is disposed so as to be brought into contact with a wall surface of the cam chamber 91. With such a configuration, a movement of the follower 94 in the longitudinal axis direction of the grasping portion 36 is prohibited, and only a rotation of the follower 94 in the circumferential direction about the longitudinal axis of the grasping portion 36 is allowed.

The driver 93 and the follower 94 disposed in the cam chamber 91 are set such that, when the driver 93 is positioned on a proximal end side defined by the communication hole 90a, a portion of the distal end surface 93a of the driver 93 and a portion of a proximal end surface 94a of the follower 94 are brought into contact with each other in a predetermined contact state, and the follower 94 is positioned in a predetermined rotation position (first rotation position) (see FIGS. 17 and 19). Then, when the driver 93 is moved toward the distal end side defined by the communication hole 90a, a contact position between the distal end surface 93a of the driver 93 and the proximal end surface 94a of the follower 94 changes so that the distal end surface 93a of the driver 93 and the proximal end surface 94a of the follower 94 are brought into face contact with each other whereby the follower 94 is rotatably moved to a predetermined rotation position (second rotation position) (see FIGS. 18 and 20).

A proximal end of the closely wound coil 53 is connected to the connecting member 94b such that the coil spring 51 is brought into a natural state when the operation follower 94 is positioned at the first rotation position. With such a configuration, the closely wound coil 53 can transmit an operation force generated when a user operates the slide member 93c from a proximal end side to a distal end side of the communication hole 90a to the coil spring 51. More specifically, an operation force generated when the user moves the slide member 93c toward the distal end side is converted into an operation force in a circumferential direction about a longitudinal axis by the cam mechanism 92 and, thereafter, the operation force is transmitted to the coil spring 51 by the closely wound coil 53. A direction of the operation force is set so as to agree with a winding direction of the coil spring 51 and the closely wound coil 53. Accordingly, a bending strength of the bending portion 7 can be changed over from a first bending strength to a second bending strength.

In other words, when an operation force in the winding direction is transmitted, the coil spring 51 is moved (deformed) in the winding direction of the coil spring 51 so that the coil spring 51 is strongly wound around an outer periphery of the treatment instrument channel 12 whereby the relative movement between the coil spring 51 and the treatment instrument channel 12 is not possible. Accordingly, a bending strength of the coil spring 51 (and the treatment instrument channel 12) deformed in a winding direction becomes higher than the bending strength when the coil spring 51 is in a natural state. As a result, the bending strength of the bending portion 7 is changed over to the second bending strength higher than the first bending strength.

The embodiment can acquire substantially the same manner of operation and advantageous effects as the above-mentioned first embodiment.

The present invention is not limited to the respective embodiments described heretofore, and various modifications and alterations are possible, and these modifications and alterations also fall within the technical scope of the present invention. For example, needless to say, the configuration of the respective embodiments and the respective modifications may be suitably combined with each other.

In the above-mentioned embodiments, the description has been made by exemplifying the endoscope which includes a bending portion bendable only in two directions, that is, upward and downward directions. However, the present invention is not limited to such an endoscope. For example, needless to say, the present invention is also applicable to an endoscope which includes a bending portion bendable only in two directions, that is, leftward and rightward directions, or an endoscope which includes a bending portion bendable in four directions, that is, upward, downward, leftward, and rightward directions.

Needless to say, the endoscope to which the present invention is applicable is not limited to a renal pelvic ureter endoscope.

What is claimed is:
1. An endoscope comprising:
   an insertion section including:
      a flexible tube portion configured to be passively bent;
      a bending portion configured to be actively bent, the bending portion being arranged distally relative to the flexible tube portion; and
      a distal end rigid piece arranged distally relative to the bending portion;
   a tube disposed in the insertion section;
   a coil helically wound around an outer periphery of the tube, the coil including a first portion fixed to the tube only at a longitudinal position corresponding to the distal end rigid piece, the coil further including a second portion provided proximally to the first portion; and
   an operation lever configured to move the second portion of the coil relative to the first portion and relative to the tube, the operation lever being configured to deform the coil so as to change a bending strength of at least the second portion of the coil.

2. The endoscope according to claim 1, wherein the second portion of the coil is configured to move in an extending direction of the coil so as to radially compress the tube.

3. The endoscope according to claim 1, wherein the second portion of the coil is configured to move in a winding direction of the coil so as to radially compress the tube.

4. The endoscope according to claim 1, further comprising a transmission member connected to the operation lever and to the coil, and configured to transmit an operation force applied to the operation lever to the second portion of the coil.

5. The endoscope according to claim 4, wherein the transmission member is a closely wound coil integrally formed with the coil in a state where the closely wound coil is wound around the outer periphery of the tube.

6. The endoscope according to claim 4, wherein the transmission member is an operation wire disposed along the tube.

7. The endoscope according to claim 4, wherein the transmission member is a transmission tube disposed so as to cover the outer periphery of the tube.

8. The endoscope according to claim 1, further comprising
an operation section connected to the insertion section,
wherein the operation lever is provided at the operation section so that a part of the operation lever protrudes from an outer surface of the operation section.

9. The endoscope according to claim 1, wherein the coil is configured to be deformed so as to change from a first bending strength with a first length to a second bending strength with a second length in at least the second portion of the coil.

10. The endoscope according to claim 9, wherein the first bending strength is smaller than the second bending strength.

11. The endoscope according to claim 10, wherein the first length is shorter than the second length.

12. The endoscope according to claim 1, wherein the operation lever is configured to one of slide in the axial direction of the insertion portion or rotate around a longitudinal direction of the tube so as to compress the second portion of the coil in the longitudinal direction of the tube.

13. The endoscope according to claim 1, wherein the operation lever is configured to one of slide in a longitudinal direction of the tube or rotate around the longitudinal direction of the tube so as to radially compress the tube.

14. The endoscope according to claim 1, wherein the coil including a third portion fixed to the operation lever, the third portion being configured to move relative to the tube.

15. The endoscope according to claim 1, wherein the operation lever includes a first lever portion and a second lever portion, and
when the coil is deformed by sliding of the first lever portion and rotation of the second lever portion.

16. The endoscope according to claim 1, wherein the first portion has a first density of turns per unit length and the second portion has a second density of turns per unit length, the second density being lower than the first density.

17. The endoscope according to claim 16, wherein the coil includes a third portion provided proximally to the second portion, the third portion has a third density of turns per unit length, the third density being higher than the second density, and the third portion is configured to move in an extending direction of the coil relative to the tube.

18. The endoscope according to claim 16, wherein the first portion has a first length, and the second portion has a second length, the second length being longer than the first length, and
the first portion has a first number of turns, and the second portion has a second number of turns, the second number of turns being larger than the first number of turns.

19. An endoscope comprising:
an insertion section including:
a bending portion configured to bend; and
a distal end rigid piece arranged distally relative to the bending portion;
a tube disposed in the insertion section;
a coil helically wound around an outer periphery of the tube, the coil including a first portion fixed to the tube only at a longitudinal position corresponding to the distal end rigid piece, the coil further including a second portion provided proximally to the first portion, and the first portion has a first density of turns per unit length and the second portion has a second density of turns per unit length, the second density being lower than the first density; and
an operation lever configured to move the second portion of the coil relative to the first portion and relative to the tube, the operation lever being configured to deform the coil so as to change a bending strength of at least the second portion of the coil.

* * * * *